(12) United States Patent
Chu

(10) Patent No.: US 9,125,716 B2
(45) Date of Patent: Sep. 8, 2015

(54) DELIVERY SLEEVE FOR PELVIC FLOOR IMPLANTS

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 885 days.

(21) Appl. No.: 12/760,043

(22) Filed: Apr. 14, 2010

(65) Prior Publication Data

US 2010/0268018 A1 Oct. 21, 2010

Related U.S. Application Data

(60) Provisional application No. 61/170,305, filed on Apr. 17, 2009.

(51) Int. Cl.
*A61F 2/00* (2006.01)
*A61F 2/02* (2006.01)

(52) U.S. Cl.
CPC .......... *A61F 2/004* (2013.01); *A61F 2250/0071* (2013.01)

(58) Field of Classification Search
CPC ... A61F 2/0004; A61F 2/0031; A61F 2/0045; A61F 2/0063; A61B 2017/00805
USPC ............................... 600/29, 30, 37
See application file for complete search history.

(56) References Cited

U.S. PATENT DOCUMENTS

| | | |
|---|---|---|
| 669,034 A | 2/1901 | Manly et al. |
| 3,123,077 A | 3/1964 | Alcamo |
| 4,324,331 A | 4/1982 | Ignasiak |
| 4,775,380 A | 10/1988 | Seedhom |
| 4,792,336 A | 12/1988 | Hlavacek et al. |
| 4,919,667 A | 4/1990 | Richmond |
| 4,998,912 A | 3/1991 | Scarbrough et al. |
| 5,013,292 A | 5/1991 | Lemay |
| 5,082,112 A | 1/1992 | Dunklee |
| 5,149,329 A | 9/1992 | Richardson |
| 5,217,466 A | 6/1993 | Hasson |
| 5,217,486 A | 6/1993 | Rice et al. |

(Continued)

FOREIGN PATENT DOCUMENTS

| | | |
|---|---|---|
| EP | 0412664 A1 | 2/1991 |
| EP | 1201189 A2 | 5/2002 |

(Continued)

OTHER PUBLICATIONS

Non-Final Office Action for U.S. Appl. No. 12/341,695, mailed Dec. 9, 2011, 19 pages.

(Continued)

*Primary Examiner* — Charles A Marmor, II
*Assistant Examiner* — Thaddeus Cox
(74) *Attorney, Agent, or Firm* — Brake Hughes Bellermann LLP

(57) ABSTRACT

An apparatus includes an implant and a sleeve. The implant has a support portion and a strap extending from the support portion. The support portion is configured to support a portion of a body of a patient. The strap is configured to be inserted into a tissue of the patient. The sleeve has a distal end portion, a proximal end portion and a tapered portion. The tapered portion of the sleeve is configured to dilate the tissue of the patient when the implant is inserted into the body of the patient. The proximal end portion of the sleeve is releasably coupled to the strap.

16 Claims, 12 Drawing Sheets

(56) References Cited

U.S. PATENT DOCUMENTS

| | | |
|---|---|---|
| 5,217,494 A | 6/1993 | Coggins et al. |
| 5,263,969 A | 11/1993 | Phillips |
| 5,356,432 A | 10/1994 | Rutkow et al. |
| 5,362,294 A | 11/1994 | Seitzinger |
| 5,383,905 A | 1/1995 | Golds et al. |
| 5,405,359 A | 4/1995 | Pierce |
| 5,425,747 A | 6/1995 | Brotz |
| 5,458,636 A | 10/1995 | Brancato |
| 5,485,917 A | 1/1996 | Early |
| 5,534,008 A | 7/1996 | Acksel |
| 5,562,689 A | 10/1996 | Green et al. |
| 5,584,859 A | 12/1996 | Brotz |
| 5,643,311 A | 7/1997 | Smith et al. |
| 5,683,402 A | 11/1997 | Cosgrove et al. |
| 5,702,397 A | 12/1997 | Goble et al. |
| 5,741,277 A | 4/1998 | Gordon et al. |
| 5,840,011 A | 11/1998 | Landgrebe et al. |
| 5,899,909 A | 5/1999 | Claren et al. |
| 5,931,855 A | 8/1999 | Buncke |
| 5,948,001 A | 9/1999 | Larsen |
| 5,976,127 A | 11/1999 | Lax |
| 6,010,447 A | 1/2000 | Kardjian |
| 6,012,580 A | 1/2000 | Peters et al. |
| 6,039,686 A | 3/2000 | Kovac |
| 6,042,534 A | 3/2000 | Gellman et al. |
| 6,042,536 A | 3/2000 | Tihon et al. |
| 6,042,592 A | 3/2000 | Schmitt |
| 6,044,847 A | 4/2000 | Carter et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,267,772 B1 | 7/2001 | Mulhauser et al. |
| 6,273,852 B1 | 8/2001 | Lehe et al. |
| 6,306,079 B1 | 10/2001 | Trabucco |
| 6,322,492 B1 | 11/2001 | Kovac |
| 6,328,686 B1 | 12/2001 | Kovac |
| 6,375,662 B1 | 4/2002 | Schmitt |
| 6,382,214 B1 | 5/2002 | Raz et al. |
| 6,406,423 B1 | 6/2002 | Scetbon |
| 6,478,727 B2 | 11/2002 | Scetbon |
| 6,491,703 B1 | 12/2002 | Ulmsten |
| 6,502,578 B2 | 1/2003 | Raz et al. |
| 6,506,190 B1 | 1/2003 | Walshe |
| 6,544,273 B1 | 4/2003 | Harari et al. |
| 6,547,800 B2 | 4/2003 | Foerster et al. |
| 6,565,580 B1 | 5/2003 | Beretta |
| 6,575,998 B2 | 6/2003 | Beyar |
| 6,582,443 B2 | 6/2003 | Cabak et al. |
| 6,592,515 B2 | 7/2003 | Thierfelder et al. |
| 6,592,610 B2 | 7/2003 | Beyar |
| 6,595,911 B2 | 7/2003 | LoVuolo |
| 6,596,001 B2 | 7/2003 | Stormby et al. |
| 6,599,235 B2 | 7/2003 | Kovac |
| 6,599,310 B2 | 7/2003 | Leung et al. |
| 6,612,977 B2 | 9/2003 | Staskin et al. |
| 6,638,209 B2 | 10/2003 | Landgrebe |
| 6,638,210 B2 | 10/2003 | Berger |
| 6,638,211 B2 | 10/2003 | Suslian et al. |
| 6,641,524 B2 | 11/2003 | Kovac |
| 6,641,525 B2 | 11/2003 | Rocheleau et al. |
| 6,648,899 B2 | 11/2003 | Kalinski et al. |
| 6,648,921 B2 | 11/2003 | Anderson et al. |
| 6,652,450 B2 | 11/2003 | Neisz et al. |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,691,711 B2 | 2/2004 | Raz et al. |
| 6,695,855 B1 | 2/2004 | Gaston |
| 6,702,827 B1 | 3/2004 | Lund et al. |
| 6,730,110 B1 | 5/2004 | Harari et al. |
| 6,746,455 B2 | 6/2004 | Beyar et al. |
| 6,752,814 B2 | 6/2004 | Gellman et al. |
| 6,755,781 B2 | 6/2004 | Gellman |
| 6,808,487 B2 | 10/2004 | Migliari |
| 6,830,052 B2 | 12/2004 | Carter et al. |
| 6,848,152 B2 | 2/2005 | Genova et al. |
| 6,881,184 B2 | 4/2005 | Zappala |
| 6,890,338 B1 | 5/2005 | Davis et al. |
| 6,908,425 B2 | 6/2005 | Luscombe |
| 6,911,003 B2 | 6/2005 | Anderson et al. |
| 6,911,034 B2 | 6/2005 | Nobles et al. |
| 6,932,759 B2 | 8/2005 | Kammerer et al. |
| 6,936,052 B2 | 8/2005 | Gellman et al. |
| 6,946,003 B1 | 9/2005 | Wolowacz et al. |
| 6,953,428 B2 | 10/2005 | Gellman et al. |
| 6,960,160 B2 | 11/2005 | Browning |
| 6,971,986 B2 | 12/2005 | Staskin et al. |
| 6,991,597 B2 | 1/2006 | Gellman et al. |
| 7,011,688 B2 | 3/2006 | Gryska et al. |
| 7,025,772 B2 | 4/2006 | Gellman et al. |
| 7,048,682 B2 | 5/2006 | Neisz et al. |
| 7,056,333 B2 | 6/2006 | Walshe |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,637 B1 | 8/2006 | Tannhauser |
| 7,090,686 B2 | 8/2006 | Nobles et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,122,039 B2 | 10/2006 | Chu |
| 7,131,943 B2 | 11/2006 | Kammerer |
| 7,131,944 B2 | 11/2006 | Jacquetin |
| 7,198,597 B2 | 4/2007 | Siegel et al. |
| 7,204,801 B2 | 4/2007 | Grocela |
| 7,204,802 B2 | 4/2007 | De Leval |
| 7,223,229 B2 | 5/2007 | Inman et al. |
| 7,226,407 B2 | 6/2007 | Kammerer et al. |
| 7,226,408 B2 | 6/2007 | Harari et al. |
| 7,229,453 B2 | 6/2007 | Anderson et al. |
| 7,235,043 B2 | 6/2007 | Gellman et al. |
| 7,244,260 B2 | 7/2007 | Koseki |
| 7,244,759 B2 | 7/2007 | Muller et al. |
| 7,267,645 B2 | 9/2007 | Anderson et al. |
| 7,291,104 B2 | 11/2007 | Neisz et al. |
| 7,351,197 B2 | 4/2008 | Montpetit et al. |
| 7,361,138 B2 | 4/2008 | Wagner et al. |
| 7,364,541 B2 | 4/2008 | Chu et al. |
| 7,402,133 B2 | 7/2008 | Chu et al. |
| 7,413,540 B2 | 8/2008 | Gellman et al. |
| 7,686,506 B2 | 3/2010 | Babkes et al. |
| 8,187,247 B2 | 5/2012 | Lornell |
| 8,491,458 B2 | 7/2013 | Chu |
| 8,517,914 B2 | 8/2013 | Anderson et al. |
| 2002/0010457 A1 | 1/2002 | Duchon et al. |
| 2002/0091373 A1 | 7/2002 | Berger |
| 2002/0128670 A1 | 9/2002 | Ulmsten et al. |
| 2002/0151909 A1 | 10/2002 | Gellman et al. |
| 2002/0156489 A1 | 10/2002 | Gellman et al. |
| 2003/0125715 A1 | 7/2003 | Kuehn et al. |
| 2003/0149334 A1 | 8/2003 | Ulmsten et al. |
| 2003/0220538 A1 | 11/2003 | Jacquetin |
| 2003/0225424 A1 | 12/2003 | Benderev |
| 2004/0006353 A1 | 1/2004 | Bosley et al. |
| 2004/0039453 A1 | 2/2004 | Anderson |
| 2004/0073234 A1 | 4/2004 | Chu et al. |
| 2004/0106847 A1 | 6/2004 | Benderev |
| 2004/0181243 A1 | 9/2004 | Chu et al. |
| 2004/0225181 A1 | 11/2004 | Chu et al. |
| 2004/0230206 A1 | 11/2004 | Gellman et al. |
| 2004/0267088 A1 | 12/2004 | Kammerer |
| 2005/0004427 A1 | 1/2005 | Cervigni |
| 2005/0004576 A1 | 1/2005 | Benderev |
| 2005/0038451 A1 | 2/2005 | Rao et al. |
| 2005/0038452 A1 | 2/2005 | Chu |
| 2005/0075660 A1 | 4/2005 | Chu et al. |
| 2005/0080317 A1 | 4/2005 | Merade |
| 2005/0090706 A1 | 4/2005 | Gellman et al. |
| 2005/0096499 A1 | 5/2005 | Li et al. |
| 2005/0101834 A1 | 5/2005 | Merade |
| 2005/0107805 A1 | 5/2005 | Bouffier et al. |
| 2005/0131392 A1 | 6/2005 | Chu et al. |
| 2005/0131393 A1 | 6/2005 | Chu et al. |

(56) References Cited

U.S. PATENT DOCUMENTS

| | | |
|---|---|---|
| 2005/0177022 A1* | 8/2005 | Chu et al. ............... 600/30 |
| 2005/0192600 A1 | 9/2005 | Nicolo et al. |
| 2005/0245787 A1 | 11/2005 | Cox et al. |
| 2005/0250978 A1 | 11/2005 | Kammerer |
| 2005/0256366 A1 | 11/2005 | Chu |
| 2005/0256530 A1 | 11/2005 | Petros |
| 2005/0261547 A1 | 11/2005 | Bouffier |
| 2005/0277807 A1 | 12/2005 | MacLean et al. |
| 2006/0015001 A1 | 1/2006 | Staskin et al. |
| 2006/0025649 A1 | 2/2006 | Smith et al. |
| 2006/0025783 A1 | 2/2006 | Smith et al. |
| 2006/0041185 A1 | 2/2006 | Browning |
| 2006/0058574 A1 | 3/2006 | Priewe et al. |
| 2006/0058575 A1 | 3/2006 | Zaddem et al. |
| 2006/0069301 A1 | 3/2006 | Neisz et al. |
| 2006/0089524 A1 | 4/2006 | Chu |
| 2006/0089525 A1 | 4/2006 | Mamo et al. |
| 2006/0122457 A1 | 6/2006 | Kovac et al. |
| 2006/0173237 A1 | 8/2006 | Jacquetin |
| 2006/0183966 A1* | 8/2006 | Neisz et al. ............... 600/30 |
| 2006/0195007 A1 | 8/2006 | Anderson et al. |
| 2006/0195010 A1 | 8/2006 | Arnal |
| 2006/0205995 A1 | 9/2006 | Browning |
| 2006/0211911 A1 | 9/2006 | Jao et al. |
| 2006/0229596 A1 | 10/2006 | Weiser et al. |
| 2006/0260618 A1 | 11/2006 | Hodroff |
| 2006/0264698 A1 | 11/2006 | Kondonis et al. |
| 2006/0287571 A1 | 12/2006 | Gozzi et al. |
| 2007/0015953 A1 | 1/2007 | Maclean |
| 2007/0055095 A1 | 3/2007 | Chu et al. |
| 2007/0123915 A1 | 5/2007 | Kammerer et al. |
| 2007/0202542 A1 | 8/2007 | Babu et al. |
| 2007/0203508 A1 | 8/2007 | White et al. |
| 2007/0276358 A1 | 11/2007 | Barzell et al. |
| 2008/0082105 A1* | 4/2008 | Chu ............... 606/99 |
| 2008/0091221 A1 | 4/2008 | Brubaker et al. |
| 2008/0287732 A1* | 11/2008 | Kuntz ............... 600/37 |
| 2009/0137944 A1 | 5/2009 | Haarala et al. |
| 2009/0171140 A1 | 7/2009 | Chu |
| 2009/0171142 A1 | 7/2009 | Chu |
| 2009/0216075 A1* | 8/2009 | Bell et al. ............... 600/37 |
| 2009/0221867 A1* | 9/2009 | Ogdahl et al. ............... 600/37 |
| 2011/0112357 A1* | 5/2011 | Chapman et al. ............... 600/37 |

FOREIGN PATENT DOCUMENTS

| | | |
|---|---|---|
| EP | 1508305 A2 | 2/2005 |
| EP | 1520554 A2 | 4/2005 |
| GB | 670349 | 4/1952 |
| WO | 98/35632 A1 | 8/1998 |
| WO | 02/78571 A2 | 10/2002 |
| WO | 03/092546 A2 | 11/2003 |
| WO | 03/096929 A1 | 11/2003 |
| WO | 2004/091442 A2 | 10/2004 |
| WO | 2005/110274 A2 | 11/2005 |
| WO | 2005/122721 A2 | 12/2005 |
| WO | 2006/046950 A1 | 5/2006 |
| WO | 2006/069078 A2 | 6/2006 |
| WO | 2006/108045 A2 | 10/2006 |
| WO | 2007/016698 A2 | 2/2007 |
| WO | 2007/019374 A2 | 2/2007 |
| WO | 2007/059199 A2 | 5/2007 |
| WO | 2007/059306 A1 | 5/2007 |
| WO | 2007/097994 A2 | 8/2007 |
| WO | 2007/149348 A2 | 12/2007 |
| WO | 2007059199 A3 | 4/2009 |
| WO | 2010/065992 A1 | 6/2010 |

OTHER PUBLICATIONS

Restriction Requirement Response for U.S. Appl. No. 12/341,695, filed Oct. 11, 2011, 2 pages.
Non-Final Office Action for U.S. Appl. No. 12/341,695, mailed May 10, 2011, 11 pages.
Non-Final Office Action for U.S. Appl. No. 12/341,695, mailed Aug. 30, 2012, 12 pages.
Non-Final Office Action Response for U.S. Appl. No. 12/341,695, filed Aug. 8, 2012, 14 pages.
Non-Final Office Action Response for U.S. Appl. No. 12/341,695, filed Nov. 30, 2012, 7 pages.
International Search Report and Written Opinion for PCT Application No. PCT/US2010/031274, mailed on Jul. 7, 2010, 15 pages.
Office Action for Japanese Application No. 2012-506235 (with Translation) mailed 12120/2013, 8 pages.
Patent Examination Report No. 1 for Australian Application No. 2010236353, mailed Jan. 30, 2014, 3 pages.
Non-Final Office Action for U.S. Appl. No. 13/867,460, mailed on Nov. 10, 2014, 9 pages.
Non-Final Office Action Response for U.S. Appl. No. 13/867,460, filed on Feb. 4, 2015, 6 pages.
Notice of Acceptance for AU Application No. 2010236353, mailed Feb. 2, 2015, 2 pages.
Response to Examination Report for AU Application No. 2010236353, filed on Jan. 28, 2015, 18 pages.
Office Action for EP Application No. 10714805.8, mailed Feb. 6, 2015, 5 pages.

* cited by examiner

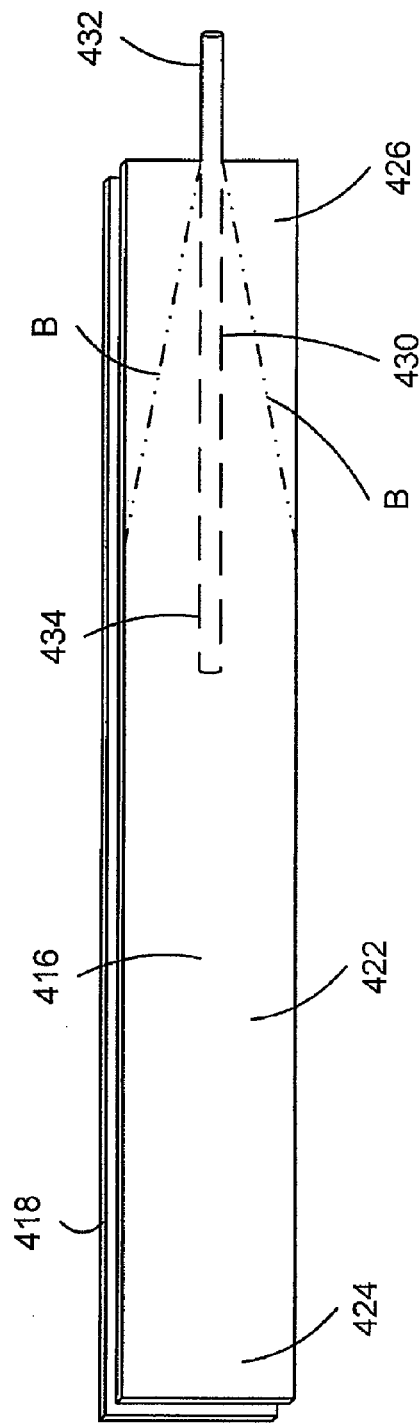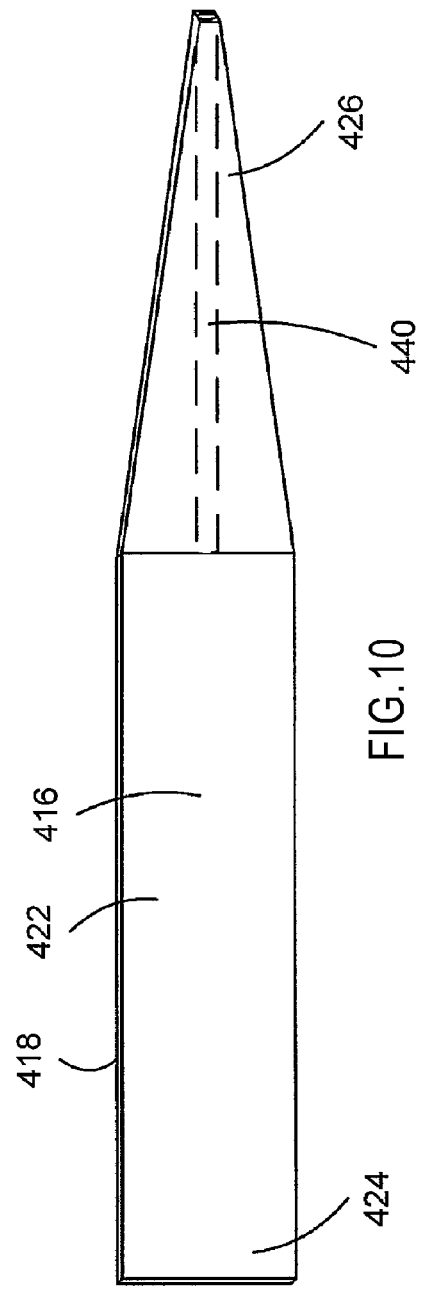
FIG.9
FIG.10

DELIVERY SLEEVE FOR PELVIC FLOOR IMPLANTS

CROSS REFERENCE TO RELATED APPLICATIONS

This application is a nonprovisional of, and claims priority to, U.S. Patent Application No. 61/170,305, filed Apr. 17, 2009, entitled "DELIVERY SLEEVE FOR PELVIC FLOOR IMPLANTS", which is incorporated by reference herein in its entirety.

BACKGROUND

The invention relates generally to medical devices and more particularly to implants and methods for delivering implants within a pelvic region of a patient to treat various pelvic dysfunctions.

A variety of medical procedures are performed to treat various female pelvic dysfunctions, including procedures to treat urinary incontinence, and to correct various prolapse conditions such as uterine prolapse, cystoceles, rectoceles, and vaginal vault prolapse.

Women often experience vaginal prolapse due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina. It is relatively common for a hysterocele and cystocele or hysterocele and rectocele, or other combinations thereof to occur at the same time. It is also common for different types of prolapse to occur in relatively quick succession.

Treatment has included suturing procedures or the use of implants for support or suspension. A hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions in the patient.

Depending on the particular condition to be treated and the implant used, pelvic floor repair can require various fixation locations within a pelvic region. For example, an implant can be secured using a number of fixation points. Sutures are often used to bridge, anchor and/or suspend the implant in place. Sutures may not provide enough surface area for tissue in-growth, and may require knotting in order to be secured. Implants formed with mesh material can provide for tissue in-growth and the width of the mesh can help prevent tissue cutting. An implant can also have roughened or tangled edges to grip surrounding tissue and hold the mesh implant in place until tissue in-growth occurs. Delivery of some implants includes the use of a sleeve to cover some or all of an implant to protect the implant from damage during delivery and to prevent premature engagement of the implant (including the roughened or tangled edges) to surrounding tissue.

Various complications can occur during a procedure to deliver and secure a pelvic implant due to, for example, space constraints for performing the implantation procedure or weak couplings between various portions of the sleeve and/or the implant. Often, implants can become damaged during delivery due to excessive stress on couplings. Thus, it would be desirable to provide improved pelvic implants and delivery aids that minimize the number of couplings and are easier to manufacture and implant within a body of a patient.

SUMMARY

An apparatus includes an implant and a sleeve. The implant has a support portion and a strap extending from the support portion. The support portion is configured to support a portion of a body of a patient. The strap is configured to be inserted into a tissue of the patient. The sleeve has a distal end portion, a proximal end portion and a tapered portion. The tapered portion of the sleeve is configured to dilate the tissue of the patient when the implant is inserted into the body of the patient. The proximal end portion of the sleeve is releasably coupled to the strap.

BRIEF DESCRIPTION OF THE DRAWINGS

FIGS. 9-10 are top views of a portion of a sleeve of an implant during manufacture, according to another embodiment.

DETAILED DESCRIPTION

Figure 1:
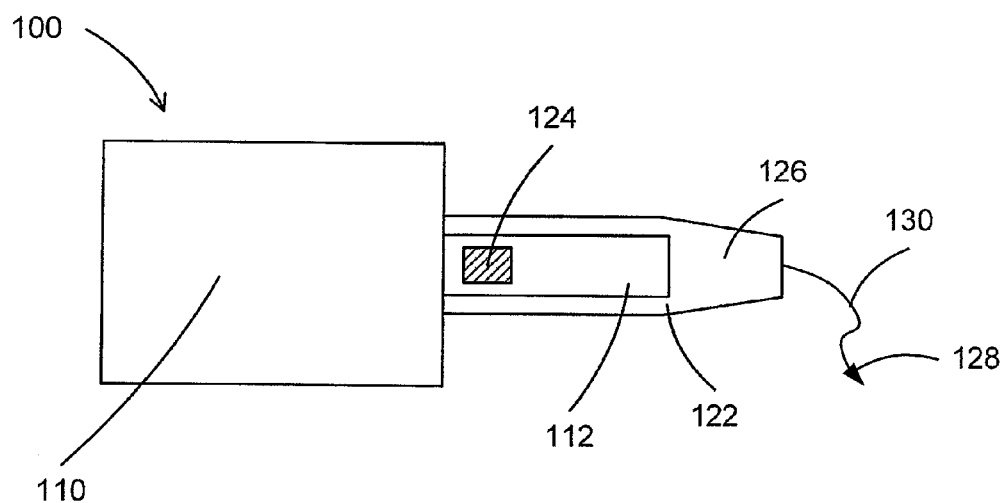
FIGS. 1 and 2 are schematic illustrations of an implant in a first configuration and a second configuration respectively, according to an embodiment.

In some embodiments, an apparatus includes an implant and a sleeve. The implant has a support portion and a strap extending from the support portion. The support portion is configured to support a portion of a body of a patient. The strap is configured to be inserted into a tissue of the patient. The sleeve has a distal end portion, a proximal end portion and a tapered portion. The tapered portion of the sleeve is configured to dilate the tissue of the patient when the implant is inserted into the body of the patient. The proximal end portion of the sleeve is releasably coupled to the strap.

In some embodiments, an apparatus includes a sleeve and a leader. The sleeve has a distal end portion and a proximal end portion. The proximal end portion of the sleeve has a width and is coupled to a strap of an implant. The distal end portion of the sleeve has a width less than the width of the proximal end portion of the sleeve. The sleeve is configured to dilate a tissue of a patient when the implant is inserted into a body of the patient. The leader is coupled to the distal end portion of the sleeve.

In some embodiments, a method of manufacturing an apparatus includes placing a first end portion of a mandrel between a first wall of a sleeve and a second wall of the sleeve. A second end portion of the mandrel is disposed apart from the first wall of the sleeve and the second wall of the sleeve. The first wall of the sleeve is then coupled to the second wall of the sleeve and an end portion of the sleeve is tapered. The mandrel is removed from between the first wall of the sleeve and the second wall of the sleeve. The sleeve defines a lumen where the mandrel was previously disposed. A leader is then coupled to the end portion of the sleeve.

As used herein, the terms proximal portion or proximal end refer to the portion or end, respectively, of a device that is closest to a medical practitioner (e.g., a physician) when performing a medical procedure, and the terms distal portion or distal end refer to the portion or end, respectively, of the device that is furthest from the physician during a medical procedure. For example, the end of an implant or sleeve first inserted inside the patient's body would be the distal end of the implant or sleeve, while the end of the implant or sleeve to enter the patient's body last would be the proximal end of the medical device.

An implant, according to an embodiment, can include one or more tangled portions. The terms "tangled" or "tangs" as used herein mean roughened or jagged edges or areas, such as can result from cutting a woven or knit mesh material. The tangled portion can be used, for example, to anchor or secure the implant to tissue. An implant, according to an embodiment, can be implanted, for example, through a vaginal incision. A procedure to deploy the implant can include a single vaginal incision, such as an anterior vaginal incision.

Implants can be delivered to a pelvic region of a patient using a variety of different delivery devices, only some examples of which are described herein. Various delivery aids are also described, some of which can be included as part of an implant (e.g., provided to a physician assembled) and some of which can be coupled to or associated with an implant just prior to implantation. Such delivery aids are typically removed after placing one or more straps of an implant at a desired tissue securement location, leaving the strap to engage the tissue and support the support portion of the implant. For example, a sleeve assembly can be used to lead an implant or a strap of an implant through a tissue in an intracorporeallocation (i.e., within the patient's body), such as the sacrospinous ligament or arcus tendineus fasciae pelvis. In other embodiments, a sleeve assembly can be used to lead an implant or a strap of an implant through a tissue and to an extracorporeal location (outside the patient's body), such as through an obturator membrane or muscle and out through an exterior incision in the patient.

Figure 2:
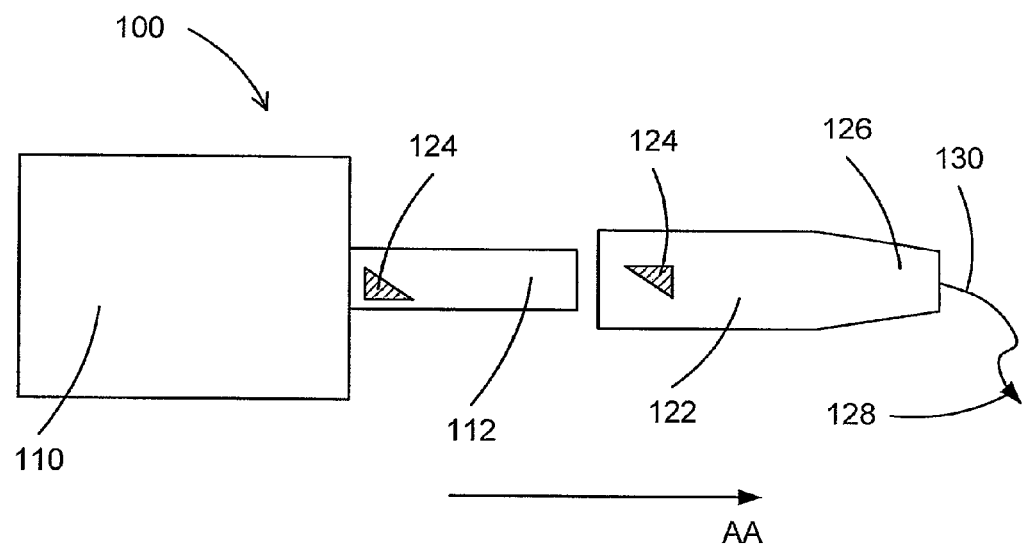

FIGS. 1 and 2 are schematic illustrations of an implant 100 in a first configuration and a second configuration, respectively, according to an embodiment. Implant 100 includes a support member 110, a strap 112, a sleeve 122, a leader 130 and a dart 128. The sleeve 122 is configured to be releasably coupled to the strap 112.

The support member 110 is configured to be placed within a body of a patient and is configured to support a portion of the body. For example, the support member 110 can be similar to the grafts disclosed in U.S. Patent Application Ser. No. 61/017,257 entitled "Apparatus and Method for Uterine Preservation," filed on Dec. 28, 2007, which is hereby incorporated by reference in its entirety. The support member 110 can be a variety of different shapes, sizes and configurations depending on the intended use for the particular implant. In some embodiments, the support member 110 can be substantially rectangular, square, oval, or elliptical. The support member 110 can be shaped and sized to support a bladder (e.g., to treat a cystocele) and/or a bladder neck and/or a uterus (e.g., to treat a hysterocele) and/or a rectum (e.g. to treat a rectocele).

The support member 110 can be formed with a mesh material to allow tissue ingrowth to the implant 100 after implantation. For example, some or all of the support member 110 can be formed with a mesh material as described in U.S. Patent Pub. 2005/0038452 A1 to Chu, the disclosure of which is hereby incorporated by reference in its entirety. In some embodiments, some or all of the support member 110 can be formed with the Advantage® Mesh or the Polyform™ Synthetic Mesh material each provided by Boston Scientific Corporation.

The strap 112 of the implant 100 is coupled to and extends from the support member 110 of the implant 100. The strap 112 is configured to support the support member 110 of the implant 100 when the strap 112 is inserted into a tissue of the patient.

In some embodiments, the strap 112 is formed with the same material as the support member 110. In other embodiments, the strap is formed with a different material than the support member. For example, the support member can be formed with a first biocompatible material and the strap can be formed with a second biocompatible material different than the first biocompatible material. In another example, the support member is formed with a biological material, and the strap can be formed with a synthetic material. The strap 112 and support member 110 can also have a different weave, pitch, texture, color, and/or pattern from each other. In some embodiments, the strap 112 is, for example, a polymer.

In some embodiments, the strap 112 is formed monolithically with the support member 110. In other embodiments, the strap is a separate component coupled to the support member. For example, the strap and the support member can be coupled in an abutting relationship, an overlapping relationship, or can be bridged. The strap can be coupled to the support member by, for example, heat bonding, gluing, using fasteners, and/or sewing. In some embodiments, the strap includes a heat seal along its length or a portion of its length to help prevent or reduce stretching of the strap.

In some embodiments the support member 110 and/or the strap 112 include the or more tangled portions (as described above). The tangs allow the implant 100 to be anchored within tissue, such as pelvic tissue, without the use of additional anchoring mechanisms or sutures. In some embodiments, an implant 100 includes tangs on an edge along an entire length of the implant 100. In other embodiments, the implant includes tangs covering substantially all of an exterior surface of the implant. In some embodiments, tangs are only on the strap 112 of the implant 100. For example, in some embodiments, the strap 112 includes a tangled portion to engage and/or help secure the implant to pelvic tissue. Pelvic tissue, as used herein, can include, for example, ligaments (such as a sacrospinous ligament), muscle (such as an obturator internus muscle or an obturator externus muscle), fascia, or any other structure or tissue within a pelvic region of a patient. In other embodiments, the implant includes anchors and/or other mechanical fasteners to secure one or more straps to the pelvic tissue. For example, a suture can be used to secure a strap or other portion of an implant to pelvic tissue.

As with the support member 110, the strap 112 can have a variety of different configurations and/or different sizes (e.g. lengths, widths), depending on the intended use for the particular implant 100 and the intended implantation site for the strap 112. For example, the length of the strap 112 can depend on the particular tissue (e.g., ligament, muscle) that the strap 112 is intended to be secured to, such that trimming of the strap 112 during or after placement can be reduced or eliminated. For example, a strap can have a length such that the strap can be placed through, and/or secured to, tissue, such as a sacrospinous ligament, but is not long enough to return back through a vaginal insertion point. In some embodiments, the strap 112 has a length such that it extends from a pelvic region through an exterior incision of the patient. In other embodiments, the strap has a length just sufficient to be secured to a target tissue site. This allows the implant to be formed with less material. The use of a strap having a length configured for the particular use can thus eliminate the need for trimming and also reduce the costs to manufacture the implant. Such embodiments of a strap can also help prevent strap stretch that can occur during insertion of the implant due to pulling on longer length strap through pelvic tissue.

While the implant 100 is shown in FIG. 1 as having a single strap 112, in other embodiments, the implant can have any number of straps depending on the particular intended use for the implant. For example, the implant can have between one and twenty straps. In some embodiments, one or more straps extend from the support member at an angle other than 90 degrees from a centerline of the support member. Such an angle of a strap can vary in different embodiments, for example, between 20 and 160 degrees from the centerline of the support member.

The sleeve 122 of the implant 100 can be used during the insertion of the implant 100 into a pelvic region to prevent the strap 112 from prematurely engaging tissue during the delivery procedure. For example, if the strap 112 includes a tangled portion, the sleeve 122 can prevent the tangs from engaging tissue as the implant 100 is being delivered into the pelvic region. Conversely, when no sleeve is coupled to the strap 112, the tangs can engage the surrounding tissue making it difficult to smoothly slide and/or adjust the strap 112. The sleeve 122 can also help in adjusting the tension of a strap 112, for example, to relieve strap tension. The sleeve 122 can also protect the strap 112 from damage during delivery.

The sleeve 122 of the implant 100 can be made of any suitable material, such as, for example, polymer, and is releasably coupled to the strap 112 by a releasable joint 124. In some embodiments, the releasable joint 124 can be similar to the releasable joints shown and described in U.S. Provisional Patent Application No. 61/120,196, filed Dec. 5, 2008 entitled "Method and Device to Deliver Pelvic Floor Implant" which is incorporated herein by reference in its entirety.

The releasable joint 124 can include a heat weld, glue, an interference fit, a controllably tearable portion, and/or mechanical engagements such as fasteners. For example, in some embodiments, a polymer sleeve 122 is heat welded to a polymer strap 112. In other embodiments, the sleeve is coupled to the strap by multiple releasable joints and/or multiple attachments of a releasable joint, such as, for example, multiple heat welds. This affords greater flexibility to the sleeve and can minimize damage to the strap when the multiple attachments of the releasable joint and/or the releasable joint is broken.

Because a releasable joint 124 is used to couple the sleeve 122 to the strap 112, the sleeve 122 is uncoupled from the strap 112 without using a tool to sever a portion of the sleeve 122 and/or strap 112. For example, the releasable joint 124 can be frangible and configured to break and/or release when a predetermined force is exerted on the releasable joint 124. For example, in some embodiments the releasable joint 124 is configured to break and/or release when a force of about 4 lbs to 6 lbs is exerted on the releasable joint 124. In other embodiments, the releasable joint is configured to break and/or release when a force greater than 6 lbs is exerted on the releasable joint. In still other embodiments, the releasable joint is configured to break and/or release when a force less than 4 lbs is exerted on the releasable joint.

The releasable joint 124 can be positioned at any portion of the sleeve 122 that overlaps the strap 112. In some embodiments, for example, the releasable joint 124 can be positioned at the portion of the strap closest to the support member 110. In embodiments where multiple attachments of the releasable joint and/or multiple releasable joints are used, the multiple joints can be placed in any position and/or any configuration along the sleeve and strap. For example, in some embodiments, the multiple releasable joints are placed along the edge of the strap and the sleeve. This positioning makes it easier for a medical practitioner to remove the sleeve from the strap once the implant is placed within a body of a patient. In other embodiments, the multiple releasable joints can be placed towards the center of the strap and the sleeve. In some embodiments, the sleeve defines a lumen that is configured to receive at least a portion of the strap.

The sleeve 122 includes a tapered portion 126 that can be used to assist in the delivery of the implant 100 to the pelvic region. The tapered portion 126 of the sleeve 122 is tapered from a larger width and/or diameter at a proximal or trailing end to a smaller width and/or diameter at a distal or leading end of the tapered portion 126. The tapered portion 126 of the sleeve 122 is configured to produce a passage through tissue to facilitate strap placement. Using a tapered portion 126 to introduce the strap 112 into a pelvic region can help reduce handling or pulling of the implant 100 itself, thereby reducing or eliminating potential damage to the implant 100. A tapered portion 126 of the sleeve 122 is used instead of a separate dilator, to reduce the number of couplings and thus reduce the chance the implant may become damaged and/or break during insertion.

The tapered portion 126 can have a variety of different configurations. For example, the tapered portion 126 can be a variety of different lengths, shapes, diameters, etc. In some embodiments, for example, the tapered portion 126 has a long, gradual taper. A long gradual taper minimizes stress as the tapered portion 126 is pulled through tissue. The tapered portion 126 can expand a passage formed by the dart 128 (as described below) during insertion through a tissue to ease the transition of the opening of the tissue to a cross-section of the sleeve 122. The tapered portion 126 of the sleeve 122 can be manufactured and/or formed by cutting, folding, thermo bond, heat pressing and/or the like, as described in further detail herein.

The sleeve 122 can be transparent, semi-transparent, colored, non-colored, or a combination thereof. The sleeve 122 can be, for example, tapered, flat, and/or tubular. In some embodiments, the sleeve 122 is substantially flat before engaging a tissue and becomes cylindrical in shape as it wraps and/or compresses around itself as it is pulled through tissue. In such embodiments, the flat sleeve 122 has a width greater than the width of the insertion point (e.g., the width of a dart 128). Because the width of the insertion point is smaller than the width of the flat sleeve, the flattened edges of the sleeve 122 are compressed to conform to the width of the insertion point and the sleeve 122 becomes cylindrical in shape as it is pulled through the insertion point and the tissue.

A sleeve 122 can be formed for example, with a clear, thin, flexible biocompatible polymer, and be configured to allow the user to examine or view the implant 100 (e.g., strap 112) disposed within the sleeve 122. After the strap 112 is positioned at a desired location within the pelvic region, the sleeve 122 can be removed from the strap 112, as described in more detail below.

In some embodiments, the sleeve 122 extends away from the support portion 110 beyond the strap 112. The sleeve 122 can thus be used to provide an extension to the strap 112 to help in the insertion process. The sleeve 122 can also help maintain the cleanliness of the strap 112 during insertion as a portion of the strap 112 that will be secured within the pelvic region will be protected within the sleeve 122.

The leader 130 is coupled to a distal end portion of the sleeve 122, and the dart 128 is coupled to a distal end portion of the leader 130. In some embodiments, the leader 130 is constructed of a biocompatible reinforced structure. In some embodiments, for example, the leader 130 can be a 7×7 stainless steel braided wire. In such embodiments, the leader 130 can also be coated with a polymer coating. A polymer coating can be used to help prevent breakage during the insertion processes and to prevent the braid from unraveling at its ends. The polymer coating also provides a smooth outer surface that minimizes the damage to tissue as the leader 130 is inserted through the tissue. In other embodiments, the leader is a suture. In such embodiments, the suture can be formed, for example, with a polymer.

The leader 130 can be coupled to the sleeve 122 by, for example, gluing, heat bonding, knotting, an interference fit, or other methods of attachment. In some embodiments, for example, a polymer coating of the leader 130 is glued to the sleeve 122 using cyanoacrylates. In other embodiments, the leader can be knotted and/or crimped within a lumen defined by the sleeve. The reinforced leader 130 withstands breakage when coupled to the sleeve 122.

The leader 130 can be any size configured to aid the insertion of the implant into a body of a patient. In some embodiments, for example, the leader has an outer diameter of about 0.016 inches. In other embodiments, the leader has an outer diameter between 0.001 inches and 0.05 inches. A small diameter increases the medical practitioner's visibility of the patient and provides the medical practitioner with increased working space within a vaginal incision. Additionally, having a long leader 130 with a small diameter while minimizing the length of the sleeve 122 having a larger diameter than the leader, increases the medical practitioner's visibility of the patient and provides the medical practitioner with increased working space within a vaginal incision. In still other embodiments, the outer diameter of the leader varies along the length of the leader. In such an embodiment, the leader can aid the tapered portion of the sleeve in dilating the tissue.

Figure 3:
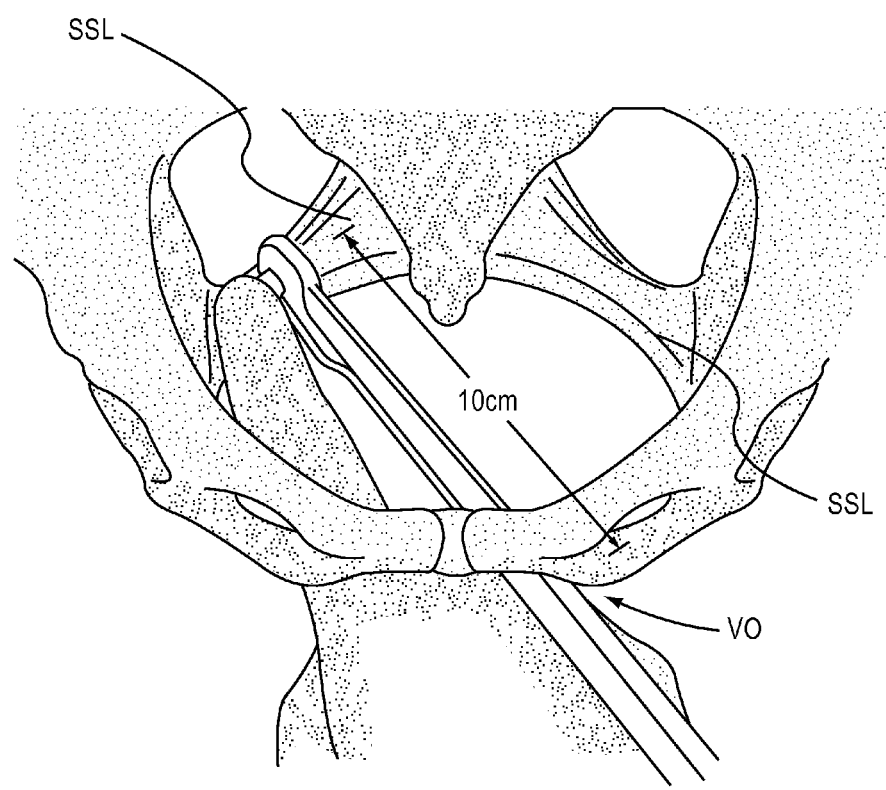
FIG. 3 is an illustration of a delivery device delivering an implant into a body of a patient, according to an embodiment.

A length of the leader 130 (measured from a distal end of the tapered portion 226 of the sleeve 122) can vary. For example, in some embodiments, the length of the leader 130 is sufficiently long to be placed through a selected tissue anchoring site (after entering the pelvic region via a vaginal incision), and passed out through the vaginal incision, without requiring the tapered portion 126 of the sleeve 122 to engage the selected tissue anchoring site (e.g., after passing through a tissue within the pelvic region). For example, the leader can be longer than the length between the sacrospinous ligament SSL and the vaginal opening VO. As shown in FIG. 3, in some embodiments, the length between the sacrospinous ligament SSL and the vaginal opening VO is approximately 10 cm in length. In such embodiments, the length of the leader 130 allows the physician to remove the dart 128 from a delivery device external to the body before the tapered portion 126 of the sleeve 122 is pulled into the tissue or ligament. This decreases the possibility of the dart 128 becoming uncoupled from the leader 130 and lost within the body.

In other embodiments, the length of the leader is sufficiently long to be placed through a selected tissue anchoring site (after entering the pelvic region via a vaginal incision), and passed out through the vaginal incision, without requiring the tapered portion of the sleeve to enter the vagina (e.g., after passing through a tissue within the pelvic region). For example, the leader can be longer than twice the length between the sacrospinous ligament SSL and the vaginal opening VO. In some embodiments, this is about 20 cm in length. Having a leader with such a length allows the leader to be threaded through the selected tissue anchoring site and passed out through the vaginal incision before the sleeve enters the vaginal incision. Thus, in an embodiment having multiple straps and leaders, the leaders can be placed in their respective anchoring sites and passed out through the vaginal incision before the implant enters the body. This increases the visibility of the medical practitioner to insert the leaders into the multiple anchoring sites within the body. The insertion and delivery of an implant using a delivery device is described in further detail herein.

The dart 128 can be formed with various biocompatible materials, such as, for example, stainless steel, or other surgical steel. In some embodiments, the dart 128 is used to associate the strap 112 of the implant 100 to a delivery device. The dart 128 is coupled to a distal end portion of the leader 130 by any suitable means. In some embodiments, for example, the dart 128 is coupled to the leader 130 by crimping, gluing, welding, and/or the like. In some embodiments, the dart 128 is crimped directly to a polymer coated leader 130. In other embodiments, the polymer coating of the leader is stripped off the portion where the dart will be coupled before crimping the dart to the leader.

In other embodiments, rather than a leader and a dart, the sleeve can include a connector portion (not shown) that can be used to associate the straps to a delivery device. In some embodiments, a loop connector is coupled to the sleeve. Such a connector or connector portion can be used to associate the sleeve to a delivery device.

The implant 100 includes a first configuration (FIG. 1) and a second configuration (FIG. 2). The implant 100 is in the first configuration when the sleeve 122 is coupled to the strap 112 by the releasable joint 124. The implant 100 is moved from the first configuration to the second configuration, by pulling the sleeve 122 with respect to the strap 112 in the direction shown by the arrow AA in FIG. 2 while holding the strap 112 in place. When the sleeve 122 is pulled with respect to the strap 112, a force is exerted on the releasable joint 124. When the force exerted is sufficient, the releasable joint 124 will break and/or release and the sleeve 122 can be removed from the strap 112. Once the sleeve 122 is removed from the strap 112, the implant 100 is in the second configuration.

In use, the implant 100 is inserted into a body of a patient while in the first configuration. In some embodiments, the implant 100 is inserted into the pelvic region of the patient. Delivery devices can be used to deliver the strap 112 of the implant 100 to and/or through a pelvic tissue, such as, for example, a levator muscle (e.g., levator ani muscle), a sacrospinous ligament, a tendineus arch of levator muscle (also referred to herein as "arcus tendineus fasciae pelvis" or "white line"), obturator muscles, an iliococcygeus muscle, and/or to other anatomical securement sites within the pelvic region of a patient. FIG. 3 illustrates a delivery device being used to deliver and insert a strap of the implant through the sacrospinous ligament SSL.

The implant 100 can be delivered using a transvaginal approach using for example, any device capable of placing and/or securing the implant 100 within the pelvic region of a patient. In one embodiment, for example, a Capio® Suture Capture Device manufactured by Boston Scientific Corporation is used. An example of such a suturing device is described in U.S. Pat. No. 5,741,277, the disclosure of which is hereby incorporated by reference in its entirety. Other types of delivery devices can alternatively be used, such as, for example, the suturing device described in U.S. Patent Pub. 2004/0181243 A1 to Chu et al., entitled "Re-shapeable Medical Device", the disclosure of which is hereby incorporated by reference in its entirety. In such a procedure, the implant 100 is inserted through, for example, a single vaginal incision. The incision can be, for example, through the anterior vaginal mucosa.

The strap 112 of the implant 100 can alternatively be implanted using, for example, a delivery needle, such as an Obtryx® Halo, Curve, Advantage® or Lynx® device each manufactured by Boston Scientific Corporation. Examples of such devices are described in U.S. Patent Pub. No. 2005/0075660 and U.S. Patent Pub. No. 2005/0177022, the entire disclosures of which are hereby incorporated by reference in their entirety.

The implant 100 can also be configured to be associated to other delivery devices not specifically described herein. In some embodiments, the strap 112 of the implant 100 itself is configured to be associated to a delivery device. For example, a connector can be coupled directly to the strap 112 for association to a delivery device, or the strap 112 can include, for example, an opening or hole configured to associate the strap 112 to a delivery device.

The strap 112 can be pulled through a pelvic tissue using. As discussed above, the tapered portion 126 of the sleeve 122 is configured to dilate or expand the tissue and provide a lead-in (e.g., passageway) for the strap 112 to be pulled through the tissue. The pelvic tissue is dilated such that the strap 112 can be pulled through the tissue, but then prolapses or retracts to a smaller size to provide a frictional interaction between the tissue and the strap 112. The strap 112 can also be flexible such that even if a width of the strap 112 is greater than a width of a corresponding passage in the tissue formed by the lead-in device (e.g., the tapered portion of the sleeve), the strap 112 can compress and/or fold to fit within the tissue, and the tissue can dilate or expand to receive the strap 112. In some embodiments, one or more straps are tapered toward their distal end, and are larger in width near the support portion, which further provides a lead-in through the tissue.

Once the strap 112 is positioned within the pelvic tissue, the sleeve 122, the leader 130 and the dart 128 can be removed from the body of the patient. This is done by pulling the sleeve with respect to the support member 110 in the direction shown by the arrow AA in FIG. 2 while holding the strap 112 in place. The strap 112 can be held in place by, for example, a finger, an instrument, or the pelvic tissue itself. When the sleeve is pulled, a force sufficient to break and/or release the releasable joint 124 is exerted on the releasable joint 124 such that the releasable joint 124 breaks. The sleeve 122 can then be removed from the strap 112 and the implant 100 moved into the second configuration. In the second configuration, the sleeve 122, the leader 130 and the dart 128 are removed from the body of the patient. The strap 112 is left within the pelvic tissue to support the support member 110 of the implant 100.

In some embodiments, once the sleeve 122 is removed from the strap 112 and the strap 112 is disposed within the pelvic tissue, the strap 112 can be further adjusted such that the implant 100 adequately supports a portion of the body of the patient. In some embodiments, after the strap 112 is disposed within the pelvic tissue, any excess portions of the strap 112 can be removed from the strap 112.

In some embodiments, a portion of the support portion 110 is separately attached to a tissue within the pelvic region. Said another way, a portion of the support portion 110 can be secured by means other than the straps. For example, a suture can be threaded through the mesh support portion 110 and attached to adjacent pelvic tissue. This can provide additional support for the support portion 110.

Figure 4:
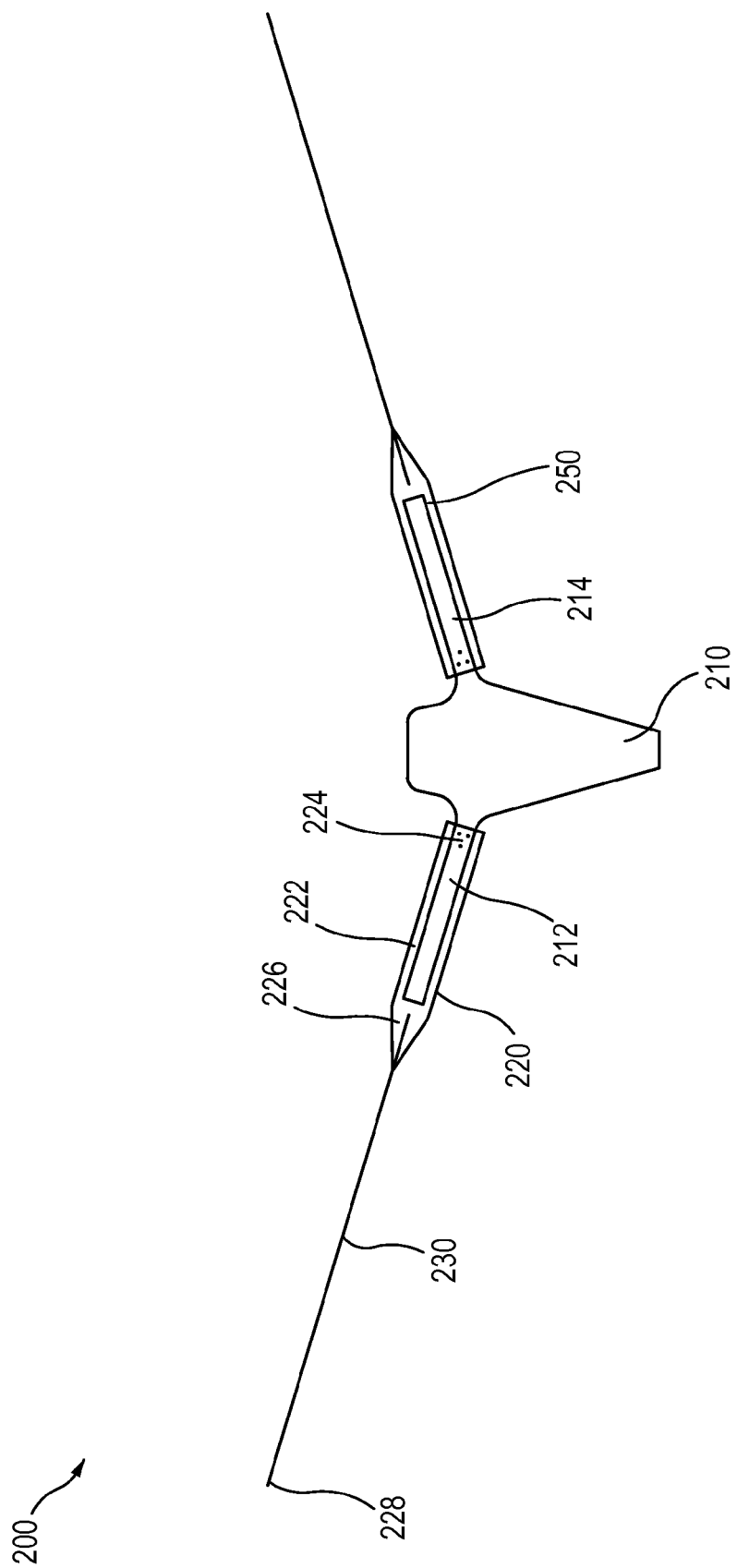
FIG. 4 is a top view of an implant, according to another embodiment.

FIG. 4 shows a top view of an implant 200, according to an embodiment. Implant 200 includes a support portion 210, a first strap 212, a first sleeve assembly 220 coupled to the first strap 212, a second strap 214, and a second sleeve assembly 250 coupled to the second strap 214.

The support portion 210 of the implant 200 is functionally similar to the support portion 110 of the implant 100 described above. Specifically, the support portion 210 of the implant 200 is configured to support a portion of a pelvic floor of a patient.

The first strap 212 and the second strap 214 are functionally similar to the strap 112 of implant 100 described above. The first strap 212 and the second strap 214 are configured to support the support portion 210 of the implant 200 when first strap 212 and the second strap 214 are disposed within a tissue of a patient.

Figure 5:
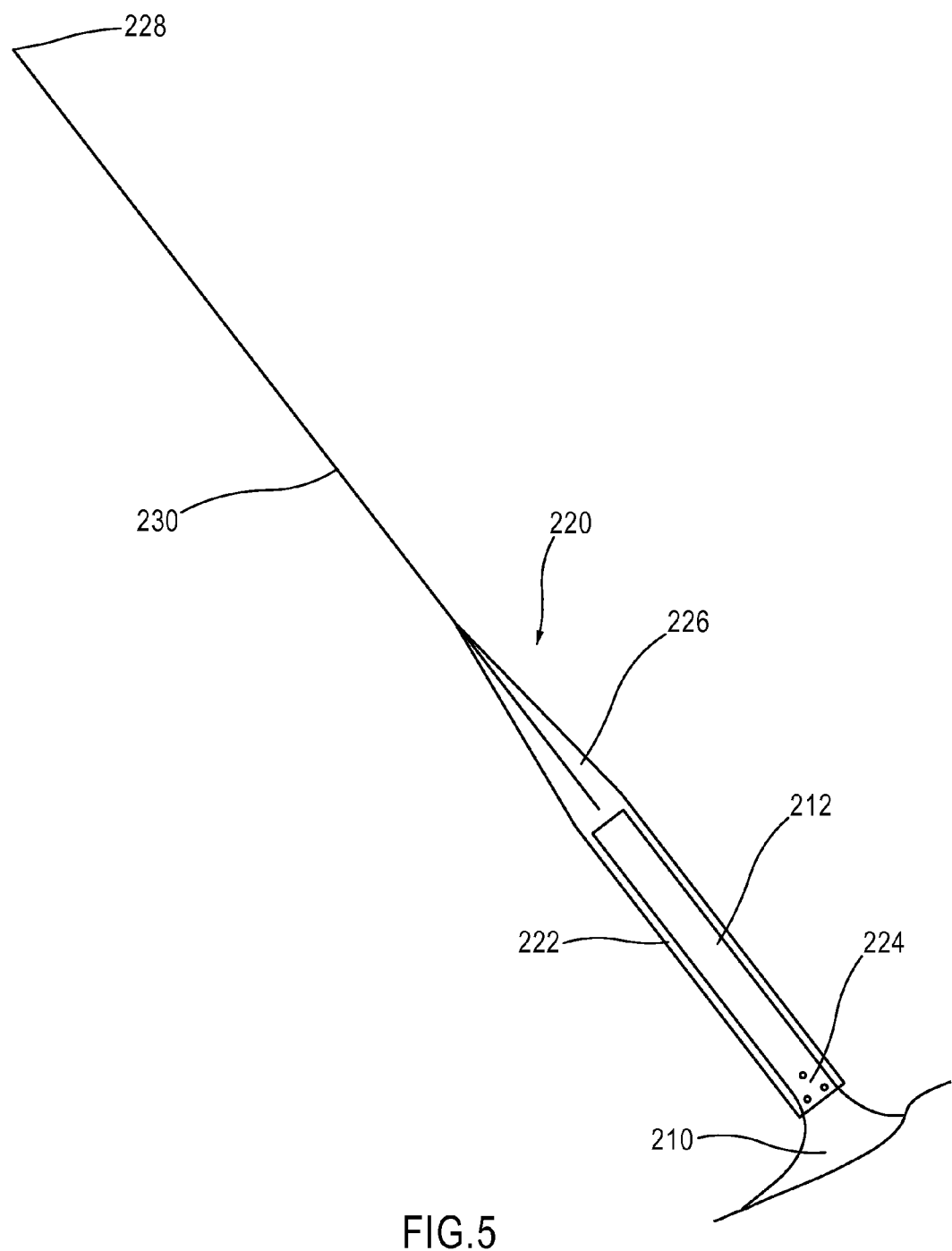
FIG. 5 is a top view of a portion of the implant of FIG. 4.

FIG. 5 shows a detailed view of the first strap 212 and the first sleeve assembly 220. The first sleeve assembly 220 includes a sleeve 222, a leader 230 and a dart 228. The sleeve 222 can be made of a material such as a polymer and defines a lumen. The sleeve 222 is configured to be coupled to at least a portion of the first strap 212, such that the portion of the first strap 212 is disposed within the lumen defined by the sleeve 222. Similar to the sleeve 122 described above, the sleeve 222 can be used during the insertion of the implant 200 into a pelvic region to prevent tangs and/or other anchoring means of the first strap 212 from prematurely engaging tissue during the delivery procedure. The leader 230 and the dart 228 are functionally similar to the leader 130 and the dart 128, respectively.

The sleeve 222 of the first sleeve assembly 220 is releasably coupled to the first strap 212 by a releasable joint 224 having three attachments. The releasable joint 224 is functionally similar to the releasable joint 124, described above. The releasable joint 224 is configured to break and/or release when a sufficient force is exerted on the releasable joint, such as, for example, about 4 lbs to 6 lbs. In this manner, the first sleeve assembly 220 can be removed from the first strap 212 when the first strap 212 is disposed within a tissue of a patient. Positioning the attachments of the releasable joint 224 close to the support portion 210 minimizes the chance that the first strap 212 will stretch and/or inadvertently uncouple from the support portion 210 when the sleeve 222 of the first sleeve assembly 220 is pulled and a force is exerted on the releasable joint, as described above.

The sleeve 222 has a tapered portion 226 similar to the tapered portion 126 of the sleeve 122 described above. The leader 230 is coupled to the tapered portion 226 of the sleeve 222, and the dart 228 is coupled to the leader 230. Similar to the tapered portion 126 of the sleeve 122, the leader 130 and the dart 128 of the implant 100 described above, the tapered portion 226 of the sleeve 222, the leader 230 and the dart 228 are used to help in the insertion of the implant 200 to the pelvic region of a patient.

In some embodiments, the first sleeve assembly 220 or a portion of the first sleeve assembly 220 is monolithically formed. For example, the leader 230 can be monolithically formed with the sleeve 222. In such an embodiment, the dart 228 is crimped or coupled to the leader 230. In other embodiments, the leader and the dart are monolithically formed with the sleeve.

The second sleeve assembly 250 is structurally and functionally similar to the first sleeve assembly 220. Additionally, the second sleeve assembly 250 is associated with the second strap 214 in a similar fashion as the first sleeve assembly 220 is associated with the first strap 212. In other embodiments, the second sleeve assembly is structurally and/or functionally different than the first sleeve assembly. For example, the length of the second sleeve assembly can be different than the length of the first sleeve assembly and/or the force needed to remove the second sleeve assembly from the second strap can be different than the force needed to remove the first sleeve assembly from the first strap.

Figure 6:
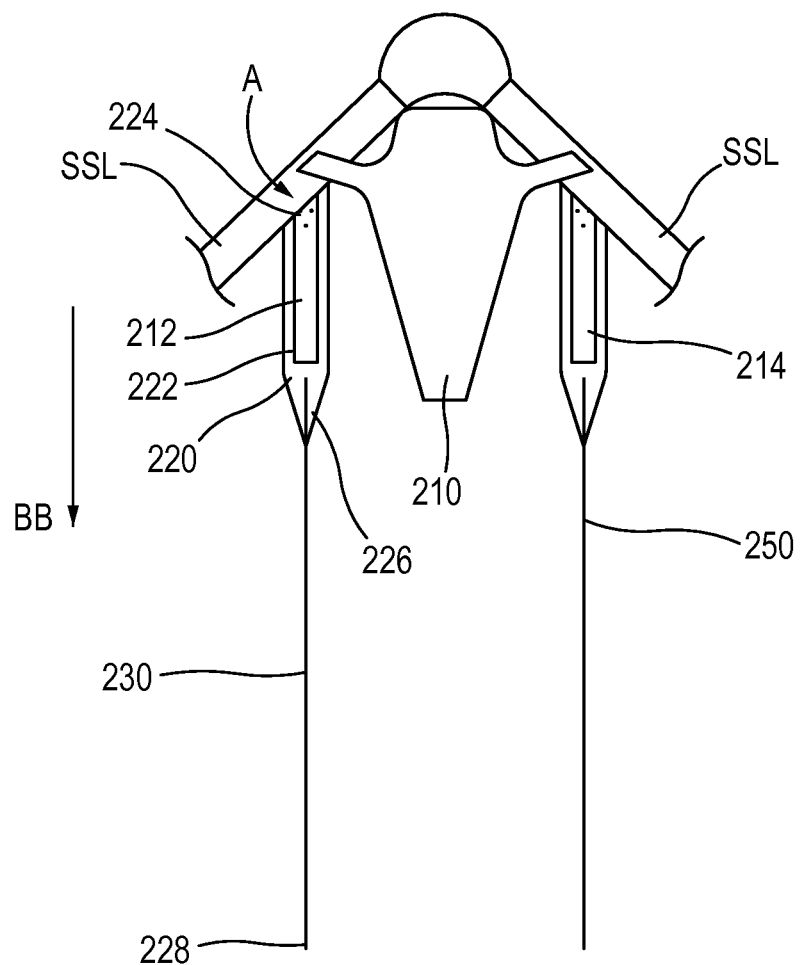
FIG. 6 is an illustration of the implant of FIG. 4 being inserted into a body of a patient.

FIG. 6 shows the implant 200 being inserted into the pelvic region of a patient. Specifically, the first strap 212 and the second strap 214 of the implant 200 are inserted into a first portion of a sacrospinous ligament SSL and a second portion of a sacrospinous ligament SSL of the patient, respectively.

The first strap 212 of the implant 200 is inserted into the first portion of the sacrospinous ligament SSL by pulling the dart 228, the leader 230, and the sleeve 222 of the first sleeve assembly 220 through the sacrospinous ligament SSL. A delivery device, such as those described above, can be used to aid in inserting the first strap 212 and the first sleeve assembly 220 into the sacrospinous ligament SSL. Once the first strap 212 (still covered by the sleeve 222) is disposed within the sacrospinous ligament, the second strap 214 can be inserted into a second portion of the sacrospinous ligament SSL using the second sleeve assembly 250, as shown in FIG. 6.

Once the first strap 212 is disposed within the sacrospinous ligament SSL, the first sleeve assembly 220 can be removed from the first strap 212. The first sleeve assembly 220 is removed from the first strap 212 by retaining the first strap 212 while pulling the first sleeve assembly 220 in a direction shown by the arrow BB in FIG. 6. The first strap 212 can be retained by placing pressure on the sacrospinous ligament SSL at a location where the first strap 212 is disposed within the sacrospinous ligament SSL between an end of the sleeve 222 of the first sleeve assembly 220 and the support member 210, such as point A in FIG. 6. This can be done by using a finger and/or other medical instrument, such as the shaft of a medical instrument and/or forceps. Alternatively, the tissue within which the first strap 212 is disposed can sufficiently retain the first strap 212. The pressure applied to point A holds the first strap 212 in place while the first sleeve assembly 220 is pulled in the direction shown by the arrow BB in FIG. 6. This causes the releasable joint 224 to break. Once the releasable joint 224 is broken, the first sleeve assembly 220 can be removed from the first strap 212. Similarly, once the second strap 214 is disposed within the sacrospinous ligament SSL, the second sleeve assembly 250 can be removed from the second strap 214 in a similar manner.

Once the first sleeve assembly 220 and the second sleeve assembly 250 are removed from the first strap 212 and the second strap 214, respectively, the first strap 212 and the second strap 214 engage the surrounding tissue and support the support portion 210 in the pelvic region of the patient. Any excess portion of the straps can be cut and/or removed.

Figure 7:
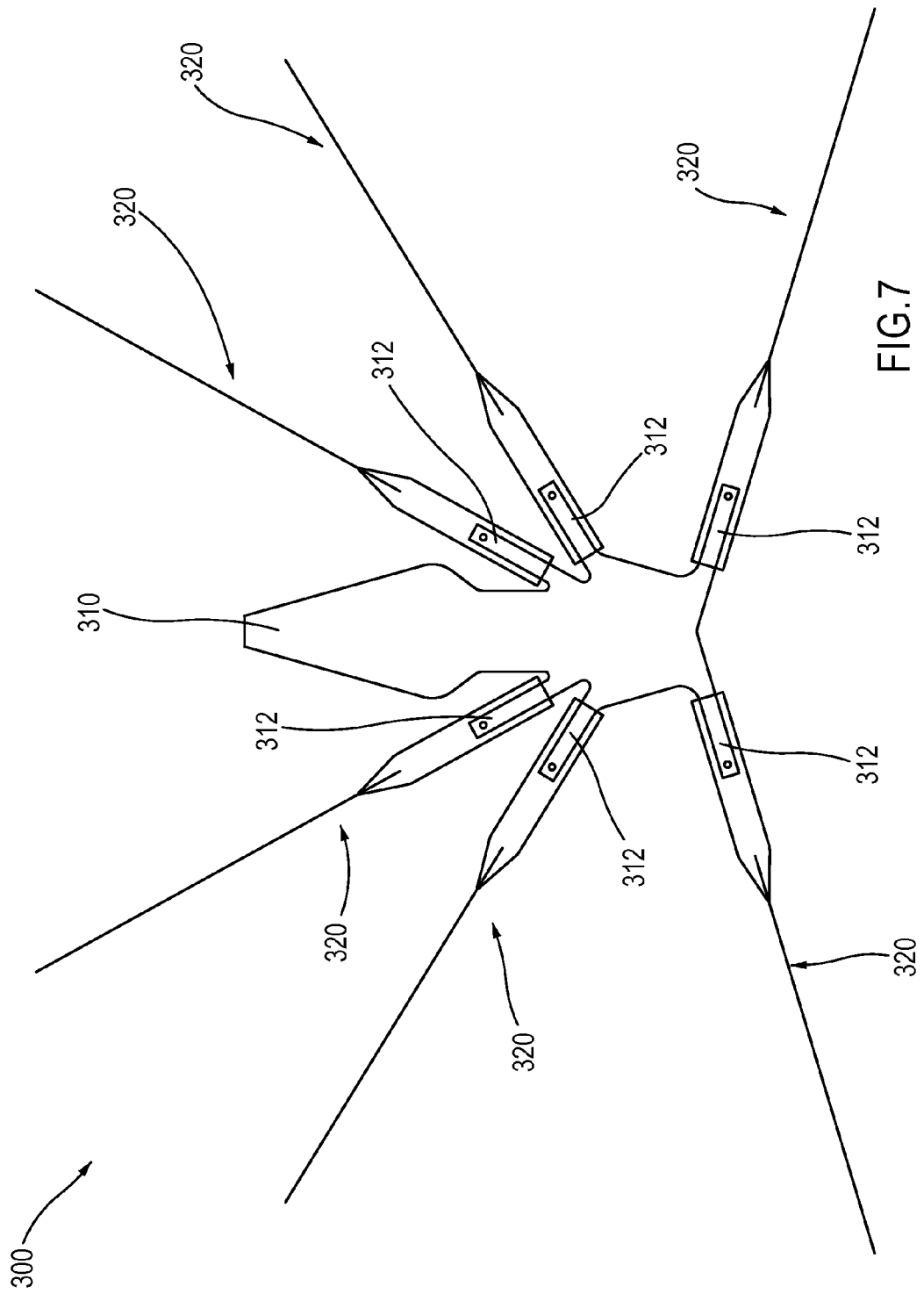
FIG. 7 is a top view of an implant, according to another embodiment.

While the implant 200 shown in FIG. 4 has two straps, in other embodiments, the implant can have any number of straps. For example, FIG. 7 shows an implant 300 having a support portion 310 and six straps 312. The implant 300 also includes six sleeve assemblies 320 configured to be coupled to the six straps 312. The straps 312 and the sleeve assemblies 320 are structurally and functionally similar to the straps and sleeve assemblies described in relation to implant 200. Having multiple straps 312 provides additional support to the support portion 310. This allows the support portion 310 to be larger and to support a larger portion of the pelvic region.

The multiple straps 312 can be inserted into a variety of tissues within the pelvic region of a patient. For example, two of the straps 312 can be placed in the sacrospinous ligament, two in the arcus tendineus fasciae pelvis and the other two in another tissue area within the pelvic region. In such an embodiment, the implant 300 can be configured to help support an anterior and/or a posterior portion of a pelvic region. In other embodiments, the number of straps and the size and shape of the support member vary depending on the application of the implant.

Figure 8:
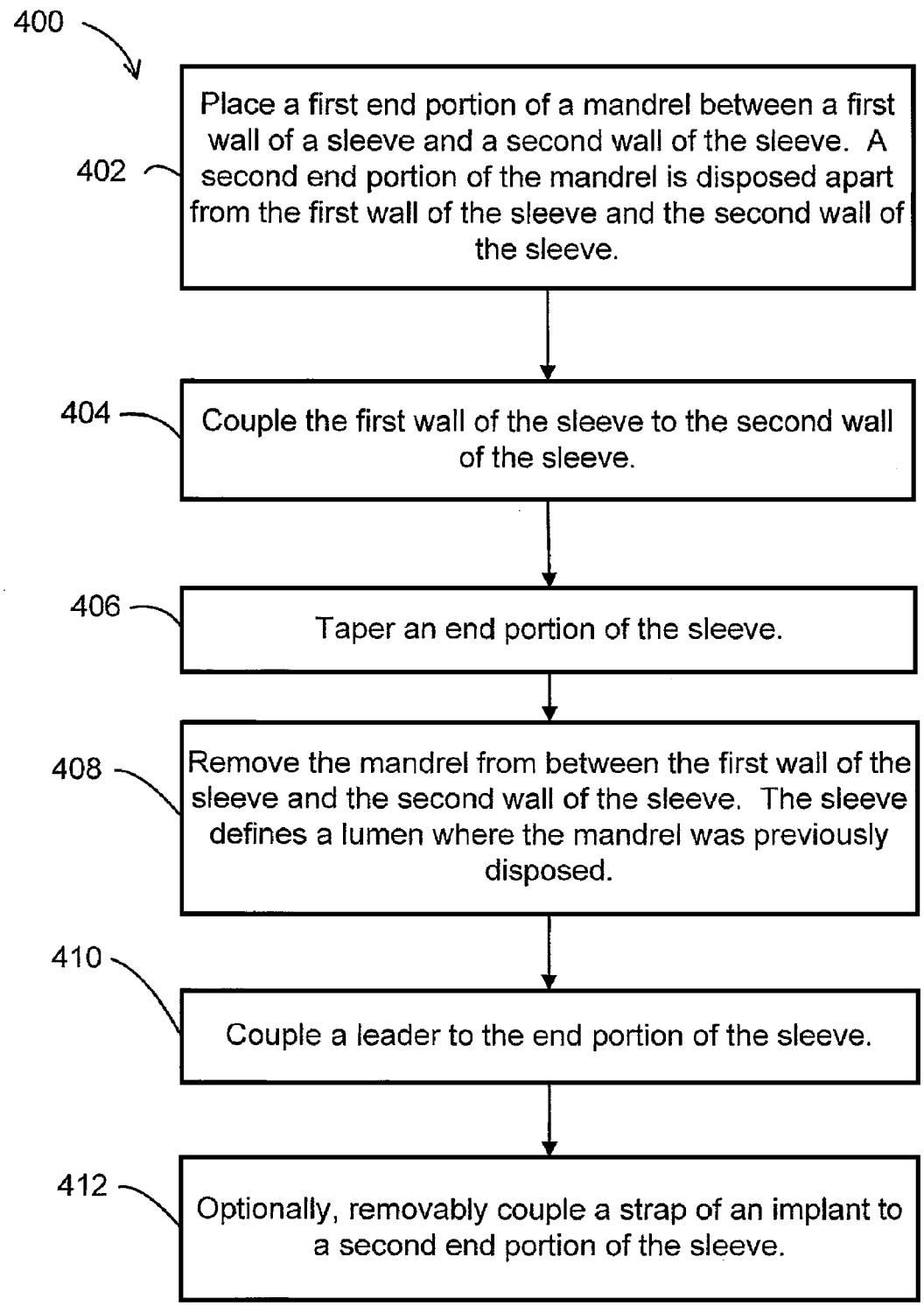
FIG. 8 is a flow chart illustrating a method of manufacturing a sleeve of an implant, according to another embodiment.

FIG. 8 is a flow chart illustrating a method 400 of manufacturing a sleeve of an implant shown in FIGS. 9 and 10, according to an embodiment. As illustrated in FIG. 9, the method 400 includes placing a first end portion 434 of a mandrel 430 between a first wall 416 of a sleeve 422 and a second wall 418 of the sleeve 422, at 402. A second end portion 432 of the mandrel 430 is disposed apart from the first wall 416 of the sleeve 422 and the second wall 418 of the sleeve 422. As shown in FIG. 9, the first end portion 434 of the mandrel 430 is disposed between the first wall 416 of the sleeve 422 and the second wall 418 of the sleeve 422 at a first end portion 426 of the sleeve 422.

The sleeve 422 is substantially similar to the sleeve 122, shown and described above, and can be made of any suitable material, such as, for example, polymer. The mandrel 430 can be constructed of any material that will not bind to the sleeve 422 when the first wall 416 of the sleeve 422 is coupled to the second wall 418 of the sleeve 422, as described in further detail herein.

With the mandrel 430 disposed between the first all 416 of the sleeve 422 and the second wall 418 of the sleeve 422, the first wall 416 of the sleeve 422 is coupled to the second wall 418 of the sleeve 422, at 404. The first wall 416 of the sleeve 422 can be coupled to the second wall 418 of the sleeve 422 using any suitable method. In some embodiments, for example, the first wall 416 of the sleeve 422 is heat bonded to the second wall 418 of the sleeve 422 creating a heat seal between the first wall 416 of the sleeve 422 and the second wall 418 of the sleeve 422. In other embodiments, the first wall of the sleeve is glued and/or crimped to the second wall of the sleeve.

The first end portion 426 of the sleeve 422 is then tapered, at 406. The first end portion 426 of the sleeve 422 can be tapered by any suitable method. In some embodiments, for example, the first end portion 426 of the sleeve 422 is tapered by cutting, folding, thermo bonding, heat pressing, and/or the like. FIG. 9 illustrates a method of tapering the first end portion 426 of the sleeve 422 by cutting. In such embodiments, once the first wall 416 of the sleeve 422 is coupled to the second wall 418 of the sleeve 422, the sleeve can be cut along the lines shown as B in FIG. 9 to form the taper. The excess portions of the sleeve 422 can be discarded.

The mandrel 430 is then removed from between the first wall 416 of the sleeve 422 and the second wall 418 of the sleeve 422, at 408. Because the mandrel 432 is constructed of a material that does not bind to the sleeve 422 when the first wall 416 of the sleeve 422 is coupled to the second wall 418 of the sleeve 422, the mandrel 432 may be removed by pulling the mandrel 432 from the sleeve 422. The sleeve 422 defines a lumen 440 where the mandrel 430 was previously disposed. FIG. 10 illustrates the tapered sleeve 422 with a lumen 440 at the first end portion 426 of the sleeve 422. In other embodiments, the mandrel 430 is removed from between the first wall of the sleeve and the second wall of the sleeve prior to the tapering of the first end portion of the sleeve.

The lumen 440 can be any shape and/or size and will correspond to the shape and size of the mandrel 430. In some embodiments, for example, the mandrel 430 is circular, and creates a circular lumen. In other embodiments, the mandrel is triangular and creates a triangular lumen. In some embodiments, the mandrel 430 can have a varying width. For example, a first portion of the mandrel 430 can have a width smaller than a width of a second portion of the mandrel 430. This creates a lumen 440 of varying width. In other embodiments, the mandrel can be shaped to form a notch and/or a protrusion in the lumen to facilitate an interference fit with a leader, as described below.

A leader (not shown in FIGS. 9 and 10) is coupled to the first end portion 426 of the sleeve 422, at 410. The leader is substantially similar to the leader 130 shown and described above. The leader can be coupled to the first end portion 426 of the sleeve 422 in any suitable manner. In some embodiments, for example, the leader is inserted into the lumen 440 defined by the first end portion 426 of the sleeve 422 and heat bonded and/or glued to the sleeve 422. The leader can be glued to the sleeve 422 using, for example, cyanoacrylates. In other embodiments, the leader is knotted or crimped to the sleeve. In still other embodiments, the leader is coupled to the first end portion of the sleeve via an interference fit within the lumen defined by the first end portion of the sleeve. In other embodiments, the leader replaces the mandrel and is heat bonded between the first wall of the sleeve and the second wall of the sleeve when the first wall of the sleeve is coupled to the second wall of the sleeve.

Optionally, a strap of an implant (not shown in FIGS. 9 and 10) is removably coupled to a second end portion 424 of the sleeve 422, at 412. In some embodiments, for example, the second end portion 424 of the sleeve 422 defines a lumen in which the strap of the implant can be inserted. The lumen of the second end portion 424 of the sleeve 422 can be formed by, for example, the use of a second mandrel and/or the like when the first wall 416 of the sleeve 422 is coupled to the second wall 418 of the sleeve 422, at 404. The strap of the implant can then be removably coupled to the second end portion 424 of the sleeve 422 by, for example, a releasable joint. The releasable joint can be similar to the releasable joints shown and described above.

Figure 11:
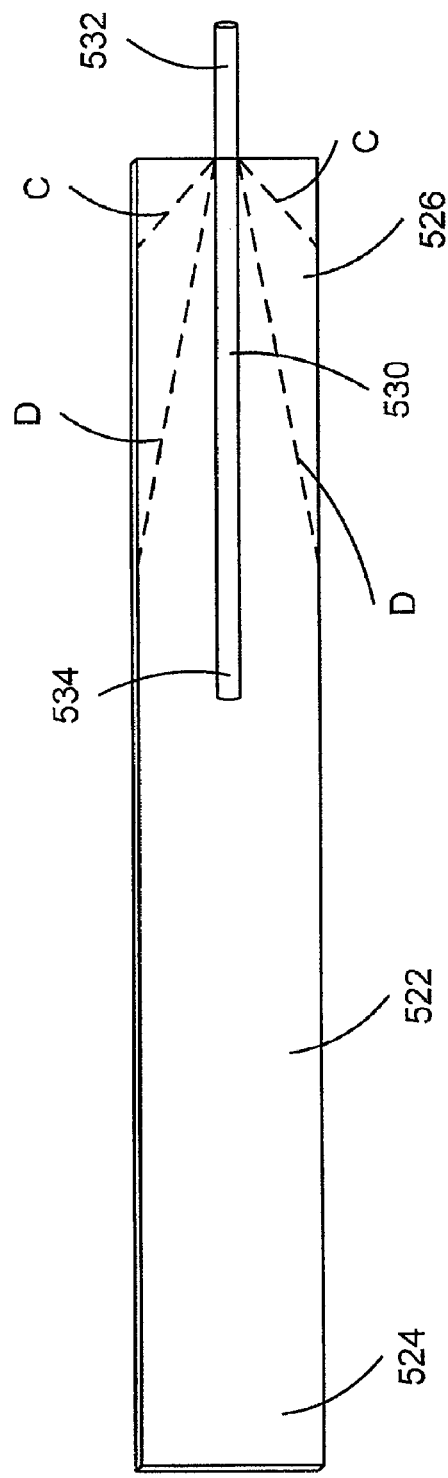
FIGS. 11-12 are top views of a portion of a sleeve of an implant during manufacture, according to another embodiment.
Figure 12:
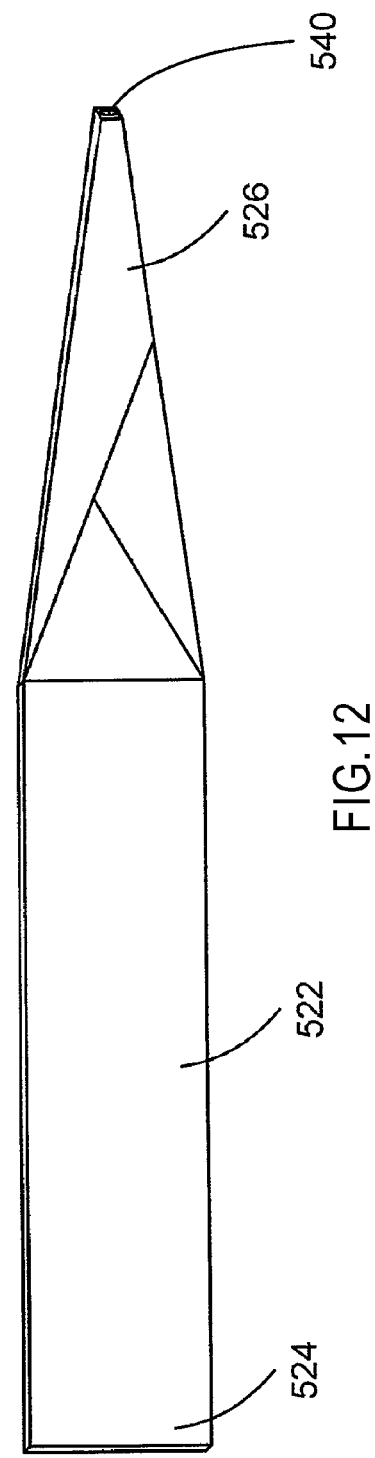

FIGS. 11-12 show a sleeve 522 in which a first end portion 526 of the sleeve 522 is tapered using a folding technique. The two walls of the sleeve 522 are first coupled together to form the sleeve 522. The taper is formed by placing a first end portion 534 of a mandrel 530 on an outside surface of the sleeve 522. A second end portion 532 of the mandrel 530 is disposed away from the sleeve 522. The sleeve 522 and the mandrel 530 are substantially similar to the sleeve 422 and the mandrel 430 shown and described above.

A portion of the first end portion 526 of the sleeve 522 is then removed. This is done by cutting the sleeve 522 along the lines shown as lines C in FIG. 11. The portion of the first end portion 526 of the sleeve 522 removed from the sleeve 522 can be discarded.

The first end portion 526 of the sleeve 522 is then folded over the first end portion 534 of the mandrel 530 at the lines shown as lines D in FIG. 11. The first end portion 526 of the sleeve 522 is folded such that two folds overlap each other as shown in FIG. 12. The two folds are then coupled to each other by, for example, heat bonding and/or gluing the folds together. The mandrel 530 is constructed of a material that does not bond to the sleeve 522 when the two folds are coupled to each other.

The mandrel 530 is then removed from underneath the two folds of the first end portion 526 of the sleeve 522. A lumen is defined by the first end portion 526 of the sleeve 522 where the mandrel 530 was disposed. Additionally, the taper is formed by the two folds as shown in FIG. 12. Similar to the sleeve 422, once the taper is formed, a leader (not shown) can be coupled to the first end portion 526 of the sleeve 522 and a strap of an implant can be releasably coupled to a second end portion 524 of the sleeve 522.

Figure 13:
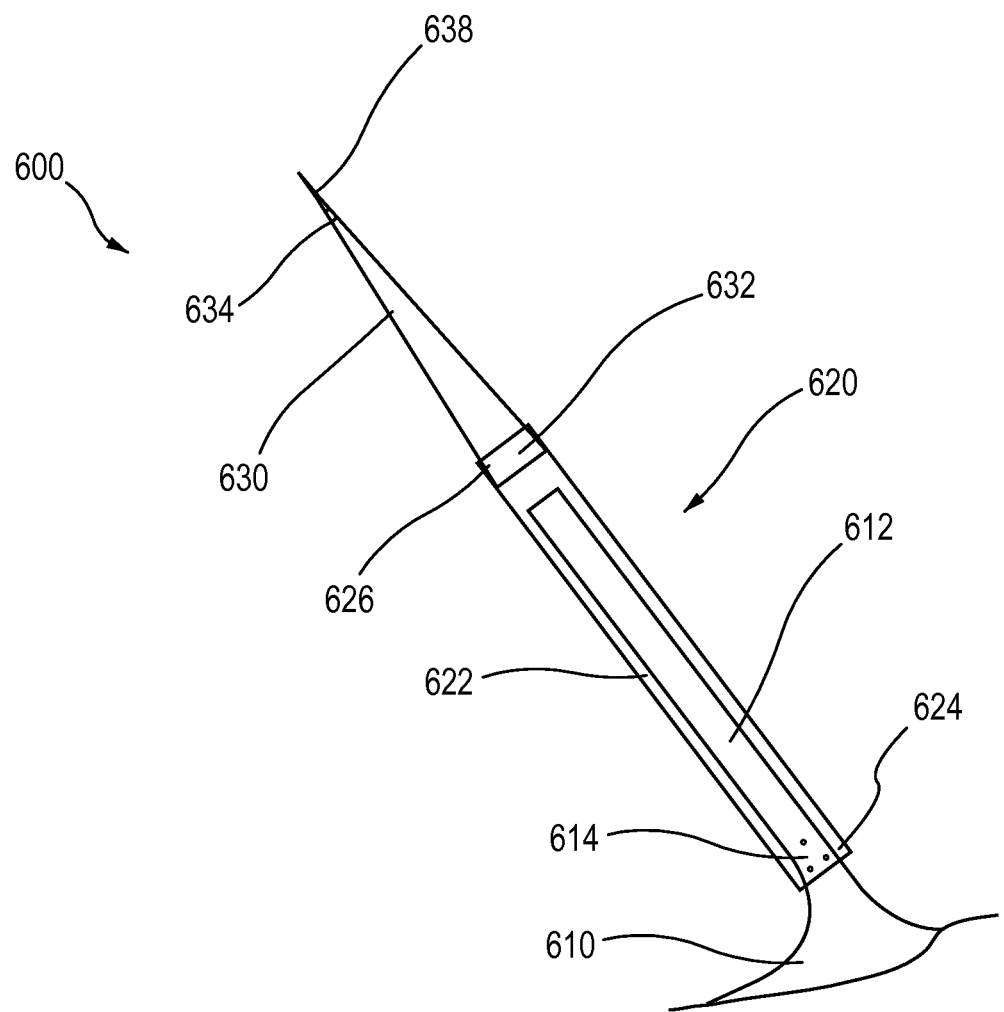
FIG. 13 is a top view of a portion of an implant, according to another embodiment.

FIG. 13 is a detailed view of a portion of an implant 600, according to another embodiment. Implant 600 includes a support portion 610, a strap 612, and a sleeve assembly 620 coupled to the strap 612. The support portion 610 of the implant 600 is structurally and functionally similar to the support portion 210 of the implant 200 described above. Specifically, the support portion 610 of the implant 600 is configured to support a portion of a pelvic floor of a patient. The strap is structurally and functionally similar to the strap 212 of implant 200 described above. The strap 612 is configured to support the support portion 610 of the implant 600 when strap 612 is disposed within a tissue of a patient.

The sleeve assembly 620 includes a sleeve 622, a leader 630, and a dart 638. The sleeve 622 can be made of a material such as a polymer and defines a lumen. The sleeve 622 includes a proximal end portion 624 and a distal end portion 626. The proximal end portion 624 of the sleeve 622 is configured to be coupled to at least a portion of the strap 612, such that the portion of the strap 612 is disposed within the lumen defined by the sleeve 622. Similar to the sleeve 222 described above, the sleeve 622 can be used during the insertion of the implant 600 into a pelvic region to prevent the strap 612 from prematurely engaging tissue during the delivery procedure.

The proximal end portion 624 of the sleeve 622 is releasably coupled to the strap 612 by a releasable joint 614 having three attachments. The releasable joint 614 is functionally similar to the releasable joint 224, described above. The releasable joint 614 is configured to break and/or release when a sufficient force is exerted on the releasable joint, such as, for example, about 4 lbs to 6 lbs. In this manner, the sleeve assembly 620 can be removed from the strap 612 when the strap 612 is disposed within a tissue of a patient. Positioning the attachments of the releasable joint 614 close to the support portion 610 minimizes the chance that the first strap 612 will stretch and/or inadvertently uncouple from the support portion 610 when the sleeve 622 of the sleeve assembly 620 is pulled and a force is exerted on the releasable joint 614, as described above.

The leader 630 includes a proximal end portion 632 and a distal end portion 634. The leader 630 is tapered from the proximal end portion 632 to the distal end portion 634. Said another way, the proximal end portion 632 of the leader 630 has a diameter larger than a diameter of the distal end portion 634 of the leader 630. The tapered leader 630 is configured to dilate or expand the tissue and provide a lead-in (e.g., passageway) for the strap 612 to be pulled through the tissue. In such embodiments, the sleeve 622 need not have a tapered portion or can have a smaller tapered portion as the tapered leader 630 assists in dilating the tissue.

The proximal end portion 632 of the leader 630 is coupled to the distal end portion 626 of the sleeve 622 by any suitable means. In some embodiments, for example, the proximal end portion 632 of the leader 630 is heat bonded, glued, and/or crimped, to the distal end portion 626 of the sleeve 622. A dart 638 is coupled to the distal end portion 634 of the leader 630. The dart 638 can be structurally and functional similar to the dart 228 and is coupled to the leader 630 in a similar manner as the dart 228 is coupled to the leader 230, shown and described above. In other embodiments, the dart is monolithically formed with the leader.

Figure 14:
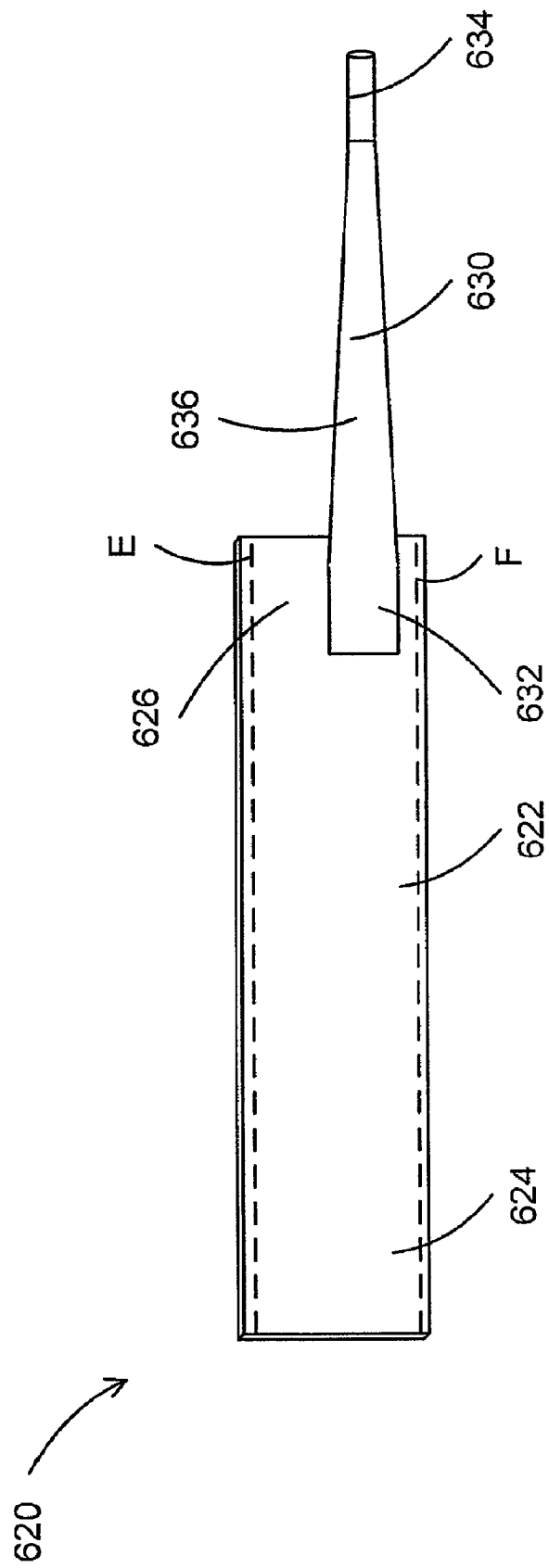
FIG. 14 is a top view of a portion of a sleeve of the implant shown in FIG. 13, during manufacture.

The sleeve assembly 620 can be manufactured by any suitable method. For example, FIG. 14 shows a portion of the sleeve assembly 620 during manufacture, according to an embodiment. In order to form the sleeve 622 and couple the proximal end portion 632 of the leader 630 to the distal end portion 626 of the sleeve 622, the proximal end portion 632 of the leader 630 is placed on top of the sleeve 622. The sleeve 622 is then wrapped around the leader 630 such that the sleeve 622 forms a cylinder around the leader 630 and line E on the sleeve 622 contacts line F on the sleeve 622. The sleeve 622 is then coupled to itself (e.g., line E is coupled to line F) and the proximal end portion 632 of the leader 630 by any suitable means such as heat bonding, gluing, crimping and/or the like. In other embodiments, a first side wall of the sleeve is wrapped around the leader and coupled to a second side wall of the sleeve to form a tube like structure and form the sleeve.

Once the leader 630 is coupled to the sleeve 622, the sleeve 622 defines a lumen in which a strap of an implant can be inserted and coupled to the proximal end portion 624 of the sleeve 622. The distal end portion 634 of the leader 630 can be coupled to a dart.

Figure 15:
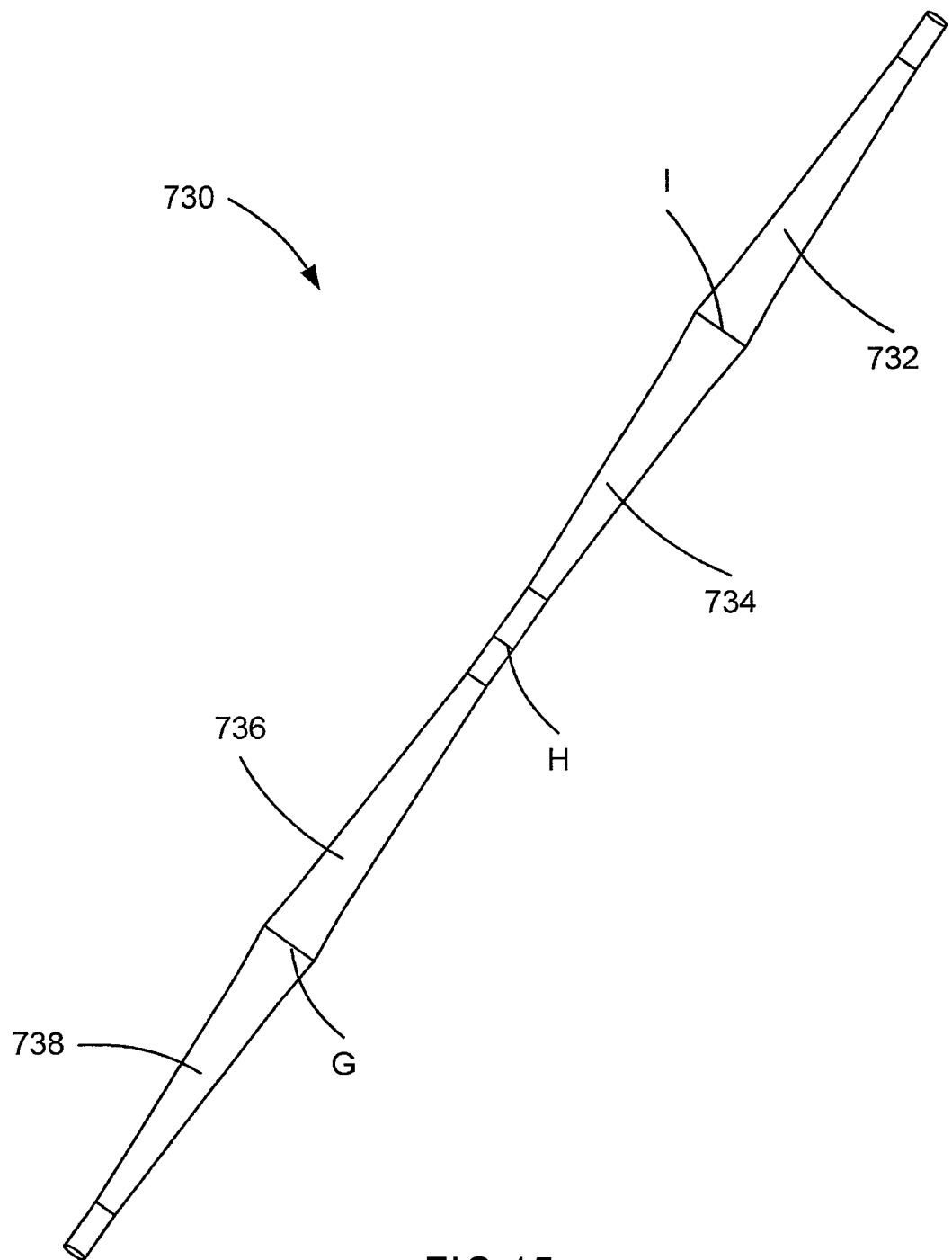
FIG. 15 is a top view of multiple leaders during manufacture, according to another embodiment.

The leader 630 of the sleeve assembly 620 can be manufactured by any suitable method. For example, FIG. 15 shows a coated braided wire 730 used to create multiple leaders 732, 734, 736, 738, according to an embodiment. In some embodiments, the braided wire 730 is stainless steel and is coated with a polymer in an extrusion process. In some embodiments, the stainless steel braided wire 730 includes tapered portions. In such embodiments, the braided wire 730 creates tapered leaders such as those shown in FIGS. 13-15). In other embodiments, the braided wire does not have tapered portions and instead has a single diameter. In such embodiments, the braded wire creates leaders without a taper such as those shown in FIGS. 1-2, 4-6 and 8-11.

Once the wire is coated with the polymer, it can be cut into multiple segments. In some embodiments, for example, four leaders 732, 734, 736, 738 are formed from a single piece of coated braided wire. For example, the coated braided wire shown in FIG. 15 can be cut at points G, H, and I to create the four leaders 732, 734, 736, 738. In other embodiments, any number of leaders can be created by from a single braided wire.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, while some embodiments are shown with a releasable joint having a single attachment and other embodiments are shown with a releasable joint having multiple attachments, any of the embodiments shown and described above, can have a releasable joint with a single attachment or a releasable joint with multiple attachments. Further, the attachments of the releasable joint can be positioned in any configuration and/or position along a sleeve covering a strap of an implant.

In some embodiments, a support portion, a strap, and/or a sleeve are provided as separate components. For example, the support portion, the strap, and the sleeve can be provided to a user (e.g., a physician) unassembled. The user can then secure the sleeve to the strap and/or the strap to the support portion to form an implant.

In some embodiments, a polymer coating of a leader can be color coded. In some embodiments, for example, each strap on an implant having multiple straps can be coupled to a leader having a different color. This aids the medical practitioner in identifying the various multiple straps and properly placing each strap in its proper location during implantation of the implant. Moreover, using the color coded leaders, a medical practitioner can easily identify which straps need adjustment when trying to properly position the implant within a body of a patient.

Although various embodiments have been described as having particular features and/or combinations of components, other embodiments are possible having a combination of any features and/or components from any of embodiments where appropriate.

In some embodiments, an apparatus includes an implant and a sleeve. The implant has a support portion configured to support a portion of a body of a patient and a strap extending from the support portion. The strap is configured to be inserted into a tissue of the patient. The sleeve has a distal end portion, a proximal end portion, and a tapered portion. The tapered portion is configured to dilate the tissue of the patient when the implant is inserted into the body of the patient. The proximal end portion of the sleeve is releasably coupled to the strap.

In some embodiments, the apparatus further includes a leader and a dart. The leader has a distal end portion and a proximal end portion. The proximal end portion of the leader is coupled to the distal end portion of the sleeve. The dart is coupled to the distal end portion of the leader.

In some embodiments, the proximal end portion of the sleeve is coupled to the strap of the implant by a releasable joint configured to break when a force is applied to the strap at a position along the strap and a force is applied to the sleeve in a direction away from the strap. In some embodiments, the proximal end portion of the sleeve defines a lumen. The strap of the implant is disposed within the lumen.

In some embodiments, the distal end portion of the sleeve defines a lumen configured receive a leader to couple the leader to the distal end portion of the sleeve. In some embodiments, the sleeve is configured to be removed from the strap of the implant when the strap is disposed within a tissue of a patient.

In some embodiments, the tapered portion of the sleeve is unitarily formed with the proximal end portion of the sleeve. In some embodiments, the apparatus further includes a leader having a proximal end portion coupled to the distal end portion of the sleeve. The proximal end portion of the leader is spaced apart from the strap of the implant.

In some embodiments, an apparatus includes a sleeve and a leader. The sleeve has a distal end portion and a proximal end portion. The proximal end portion of the sleeve has a width and is coupled to a strap of an implant. The distal end portion of the sleeve has a width less than the width of the proximal end portion of the sleeve. The sleeve is configured to dilate a tissue of a patient when the implant is inserted into a body of the patient. The leader is coupled to the distal end portion of the sleeve.

In some embodiments, the proximal end portion of the sleeve is coupled to the strap of the implant by a releasable joint. In some embodiments, the proximal end portion of the sleeve is coupled to the strap of the implant by a releasable joint configured to break when a force is applied to the strap at a position along the strap and the sleeve is pulled in a direction away from the strap.

In some embodiments, the leader includes a proximal end portion and a distal end portion. The proximal end portion of the leader is coupled to the distal end portion of the sleeve. The distal end portion of the leader is coupled to a dart configured to penetrate the tissue of the patient.

In some embodiments, the width of the distal end portion of the sleeve is substantially equal to a width of the leader. In some embodiments, the leader is heat bonded to the sleeve. In some embodiments, the leader is coupled to the sleeve using a cyanoacrylate. In some embodiments, the sleeve is configured to be removed from the strap of the implant after the implant is inserted into the body of the patient.

In some embodiments, the sleeve includes a middle portion having a width substantially equal to the width of the proximal end portion of the sleeve. The width of the sleeve gradually decreases from the width of the middle portion of the sleeve to the width of the distal end portion of the sleeve between the middle portion of the sleeve and the distal end portion of the sleeve.

In some embodiments, a proximal end of the leader is coupled to the distal end portion of the sleeve. In some embodiments, a proximal end of the leader is spaced apart from the proximal end portion of the sleeve. In some embodiments, the leader is spaced apart from the implant. In some embodiments, the leader is coupled to the implant via the sleeve.

In some embodiments, a method includes placing a first end portion of a mandrel between a first wall of a sleeve and a second wall of the sleeve. A second end portion of the mandrel is disposed apart from the first wall of the sleeve and the second wall of the sleeve. The first wall of the sleeve is coupled to the second wall of the sleeve. An end portion of the sleeve is tapered. The mandrel is removed from between the first wall of the sleeve and the second wall of the sleeve. The sleeve defines a lumen where the mandrel was previously disposed. A leader is coupled to the end portion of the sleeve.

In some embodiments, the tapering of the end portion of the sleeve includes cutting the end portion of the sleeve at an angle relative to a longitudinal axis defined by the sleeve to form the taper. In some embodiments, the tapering of the end portion of the sleeve includes folding a first flap of the sleeve onto a second flap of the sleeve and coupling the first flap to the second flap.

In some embodiments, the coupling of the leader to the end portion of the sleeve includes inserting the leader into the lumen defined by the sleeve and heat bonding the leader to the sleeve. In some embodiments, the coupling of the leader to the end portion of the sleeve includes inserting the leader into the lumen defined by the sleeve such that the lumen defined by the sleeve retains the leader via an interface fit. In some embodiments, the end portion of the sleeve is a first end portion, the method further includes removably coupling a strap of an implant to a second end portion of the sleeve.

What is claimed is:

1. An apparatus, comprising:
   an implant having a support portion configured to support a portion of a body of a patient and a strap extending from the support portion, the strap configured to be inserted into a tissue of the patient, the strap having a proximal end portion and a distal end portion, the proximal end portion of the strap being coupled to the support portion;
   a sleeve having a distal end portion, a proximal end portion, and a tapered portion, the tapered portion being configured to dilate the tissue of the patient when the implant is inserted into the body of the patient, the proximal end portion of the sleeve being releasably coupled to the proximal end portion of the strap via a releasable joint positioned between the proximal end portion of the sleeve and the proximal end of the strap, the sleeve defining a lumen, the strap being disposed within the lumen of the sleeve; and
   a leader including an elongate structure having a first end portion and a second end portion, the first end portion of the leader being coupled to the sleeve, at least a portion of the leader being disposed within the lumen defined by the sleeve, the second end portion of the leader being disposed outside the lumen defined by the sleeve and apart from the implant,
   wherein the releasable joint is configured to break when a force is applied to the strap at a position along the strap and a force is applied to the sleeve in a direction away from the strap.

2. The apparatus of claim 1, further comprising:
   a dart coupled to the second end portion of the leader.

3. The apparatus of claim 1, wherein the releasable joint includes a plurality of attachments.

4. The apparatus of claim 1, wherein the sleeve is configured to be removed from the strap of the implant when the strap is disposed within a tissue of a patient.

5. The apparatus of claim 1, wherein the tapered portion of the sleeve is unitarily formed with the proximal end portion of the sleeve.

6. The apparatus of claim 1, wherein a proximal end of the leader is disposed within the lumen of the sleeve at a distance away from the distal end portion of the strap, the distal end portion of the strap being disposed within the lumen of the sleeve.

7. The apparatus of claim 1, wherein only the first end portion of the leader is coupled to the distal end portion of the sleeve.

8. The apparatus of claim 1, further comprising a dart coupled to the second end portion of the leader, the distal end portion of the sleeve having a first configuration and a second configuration, the first configuration being substantially flat having a width greater than a width of the dart, the second configuration being cylindrical having a width substantially same as the width of the dart.

9. The apparatus of claim 1, wherein the strap defines at least one tang, and the strap is disposed within the lumen of the sleeve such that the sleeve covers the at least one tang.

10. An apparatus, comprising:
    a sleeve having a distal end portion and a proximal end portion, the proximal end portion of the sleeve having a width, the proximal end portion of the sleeve being coupled to a proximal end portion of a strap of an implant via a releasable joint, the distal end portion of the sleeve having a width less than the width of the proximal end portion of the sleeve, the sleeve being configured to dilate a tissue of a patient when the implant is inserted into a body of the patient, the sleeve defining a lumen configured to receive the strap such that the sleeve covers the strap;
    a leader including a suture or wire having a distal end portion and a proximal end portion, the proximal end portion of the leader being coupled to the distal end portion of the sleeve, at least a portion of the leader being disposed within the lumen defined by the sleeve, the distal end portion of the leader being disposed outside the lumen defined by the sleeve, the proximal end portion of the leader being disposed a distance away from a distal end portion of the strap, wherein the releasable joint is configured to break when a force is applied to the strap at a position along the strap and the sleeve is pulled in a direction away from the strap.

11. The apparatus of claim 10, wherein the releasable joint includes two or more attachments between the proximal end portion of the sleeve and the proximal end portion of the strap.

12. The apparatus of claim 10, wherein the distal end portion of the leader is coupled to a dart configured to penetrate the tissue of the patient.

13. The apparatus of claim 10, wherein the width of the distal end portion of the sleeve is substantially equal to a width of the leader.

14. The apparatus of claim 10, wherein the leader is coupled to the implant via the sleeve.

15. The apparatus of claim 10, wherein only the proximal end portion of the leader is coupled to the distal end portion of the sleeve.

16. The apparatus of claim 10, further comprising a dart coupled to the distal end portion of the leader, the distal end portion of the sleeve having a first configuration and a second configuration, the first configuration being substantially flat having a width greater than a width of the dart, the second configuration being cylindrical having a width substantially same as the width of the dart.

* * * * *